United States Patent
Merlin et al.

(10) Patent No.: US 10,477,568 B2
(45) Date of Patent: Nov. 12, 2019

(54) METHODS AND APPARATUS FOR MULTIPLE USER UPLINK

(71) Applicant: QUALCOMM Incorporated, San Diego, CA (US)

(72) Inventors: Simone Merlin, San Diego, CA (US); Alfred Asterjadhi, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 80 days.

(21) Appl. No.: 15/364,196

(22) Filed: Nov. 29, 2016

(65) Prior Publication Data
US 2017/0164392 A1    Jun. 8, 2017

Related U.S. Application Data

(60) Provisional application No. 62/262,312, filed on Dec. 2, 2015.

(51) Int. Cl.
*H04W 72/12* (2009.01)
*H04W 28/06* (2009.01)

(52) U.S. Cl.
CPC ....... *H04W 72/1268* (2013.01); *H04W 28/06* (2013.01); *H04W 72/1289* (2013.01)

(58) Field of Classification Search
CPC ......... H04W 72/1268; H04W 72/1289; H04W 28/06; H04W 84/12; H04W 72/0413
(Continued)

(56) References Cited

U.S. PATENT DOCUMENTS 9,351,333 B1 *   5/2016  Zhang ................ H04W 84/12
2006/0056443 A1 * 3/2006  Tao ..................... H04L 1/1628
                                                    370/462
(Continued)

FOREIGN PATENT DOCUMENTS

WO    WO-2015031443    3/2015

OTHER PUBLICATIONS

Al-Ghazu, A Study of the Next WLAN Standard IEEE 802.11ac Physical Layer, Jan. 2013, KTH School of Electrical Engineering (EE) Signal Processing (Year: 2013).*

(Continued)

*Primary Examiner* — Paul H Masur
*Assistant Examiner* — Michael K Phillips
(74) *Attorney, Agent, or Firm* — Paradice and Li LLP

(57) ABSTRACT

The disclosure provides methods and apparatuses for multiple user uplink. One aspect of the disclosure provides a method for wireless communication. The method comprises receiving a trigger frame from an access point indicating a target transmission duration for transmission of a physical layer (PHY) service data unit (PSDU) to the access point. The method also comprises generating an aggregated medium access control (MAC) packet data unit (A-MPDU) frame comprising at least one A-MPDU subframe, the A-MPDU frame having a first length, determining whether an additional A-MPDU subframe having a second length may be added to the A-MPDU frame based at least in part on the first length, the second length, and the target transmission duration, and including one or more padding subframes in the A-MPDU frame based at least in part on a comparison between the first length and the target transmission duration.

42 Claims, 17 Drawing Sheets

(58) Field of Classification Search
CPC ......... H04W 72/0446; H04W 72/1284; H04W 72/121; H04W 88/08; H04W 72/12; H04W 52/146; H04W 88/02; H04W 72/04; H04W 72/0406; H04W 74/06; H04B 7/0413
See application file for complete search history.

(56) References Cited

U.S. PATENT DOCUMENTS

| | | | |
|---|---|---|---|
| 2014/0036895 A1 | 2/2014 | Liu et al. | |
| 2015/0055516 A1* | 2/2015 | Smadi | H04W 72/1215 370/280 |
| 2015/0063190 A1* | 3/2015 | Merlin | H04L 5/0037 370/312 |
| 2015/0063191 A1* | 3/2015 | Merlin | H04L 47/12 370/312 |
| 2015/0063257 A1* | 3/2015 | Merlin | H04L 47/12 370/329 |
| 2015/0063291 A1 | 3/2015 | Merlin et al. | |
| 2015/0063318 A1* | 3/2015 | Merlin | H04L 47/12 370/336 |
| 2015/0139209 A1* | 5/2015 | Park | H04W 74/08 370/338 |
| 2016/0043855 A1* | 2/2016 | Seok | H04L 5/0055 370/330 |
| 2016/0057657 A1* | 2/2016 | Seok | H04L 69/324 370/476 |
| 2016/0088602 A1* | 3/2016 | Seok | H04L 5/0055 370/338 |
| 2016/0360443 A1* | 12/2016 | Hedayat | H04B 7/0452 |
| 2017/0245306 A1* | 8/2017 | Kim | H04W 74/0833 |
| 2017/0272138 A1* | 9/2017 | Chun | H04L 29/08 |
| 2018/0007561 A1* | 1/2018 | Adachi | H04W 16/28 |
| 2018/0020411 A1* | 1/2018 | Itagaki | H04W 52/242 |

OTHER PUBLICATIONS

Ding G., "Duration and MAC Padding for UL MU PPDUs, 11-15-0617-00-00 ax-Duration-and-Mac-Padding-for-Ul-mu-ppdus", IEEE Draft; 11-15-0617-00-00AX-Duration-and-MAC-Padding-for-UL-MU-PPDUs, IEEE-SA Mentor, Piscataway, NJ USA, vol. 802 .11ax, May 11, 2015, XP068094491, pp. 1-15.

International Search Report and Written Opinion—PCT/US2016/064236—ISA/EPO—dated Mar. 14, 2017.

Robert Stacey (Intel): "Proposed TGac Draft Amendment ; 11-10-1361-01-00ac-proposed-tgac-draft-amendment", IEEE Draft; 11-10-1361-01-00AC-Proposed-TGAC-Draft-Amendment, IEEE-SA Mentor, Piscataway, NJ USA, vol. 802.11ac, No. 1, Nov. 11, 2010 (Nov. 11, 2010), pp. 1-130, XP017675819.

* cited by examiner

METHODS AND APPARATUS FOR MULTIPLE USER UPLINK

CROSS REFERENCE TO RELATED APPLICATIONS

This application claims priority to U.S. Provisional Application No. 62/262,312, filed Dec. 2, 2015, and entitled "METHODS AND APPARATUS FOR MULTIPLE USER UPLINK." The disclosure of this prior application is considered part of this application, and is hereby incorporated by reference in its entirety.

FIELD

Certain aspects of the present disclosure generally relate to wireless communications, and more particularly, to methods and apparatus for multiple user uplink communication in a wireless network.

BACKGROUND

In many telecommunication systems, communications networks are used to exchange messages among several interacting spatially-separated devices. Networks may be classified according to geographic scope, which could be, for example, a metropolitan area, a local area, or a personal area. Such networks may be designated respectively as a wide area network (WAN), metropolitan area network (MAN), local area network (LAN), or personal area network (PAN). Networks also differ according to the switching/routing technique used to interconnect the various network nodes and devices (e.g., circuit switching vs. packet switching), the type of physical media employed for transmission (e.g., wired vs. wireless), and the set of communication protocols used (e.g., Internet protocol suite, SONET (Synchronous Optical Networking), Ethernet, etc.).

Wireless networks are often preferred when the network elements are mobile and thus have dynamic connectivity needs, or if the network architecture is formed in an ad hoc, rather than fixed, topology. Wireless networks employ intangible physical media in an unguided propagation mode using electromagnetic waves in the radio, microwave, infra-red, optical, etc. frequency bands. Wireless networks advantageously facilitate user mobility and rapid field deployment when compared to fixed wired networks.

In order to address the issue of increasing bandwidth requirements that are demanded for wireless communications systems, different schemes are being developed to allow multiple user terminals to communicate with a single access point by sharing the channel resources while achieving high data throughputs. With limited communication resources, it is desirable to reduce the amount of traffic passing between the access point and the multiple terminals. For example, when multiple terminals send uplink communications to the access point, it is desirable to minimize the amount of traffic to complete the uplink of all transmissions. Thus, there is a need for an improved protocol for uplink transmissions from multiple terminals.

SUMMARY

Various implementations of systems, methods and devices within the scope of the appended claims each have several aspects, no single one of which is solely responsible for the desirable attributes described herein. Without limiting the scope of the appended claims, some prominent features are described herein.

One aspect of the disclosure provides a method for wireless communication. The method comprises receiving, at a user terminal, a trigger frame from an access point indicating a target transmission duration for transmission of a physical layer (PHY) service data unit (PSDU) to the access point. The method further comprises generating an aggregated medium access control (MAC) packet data unit (A-MPDU) frame comprising at least one A-MPDU subframe, the A-MPDU frame having a first length. The method further comprises determining whether an additional A-MPDU subframe having a second length may be added to the A-MPDU frame based at least in part on the first length, the second length, and the target transmission duration. The method further comprises including one or more padding subframes in the A-MPDU frame based at least in part on a comparison between the first length and the target transmission duration. The method further comprises generating the PSDU, the PSDU including the A-MPDU frame. The method further comprises transmitting the generated PSDU from the user terminal over the target transmission duration.

Another aspect of the disclosure provides a user terminal for wireless communication. The user terminal comprises a receiver configured to receive a trigger frame from an access point indicating a target transmission duration for transmission of a physical layer (PHY) service data unit (PSDU) to the access point. The user terminal further comprises a processor configured to generate an aggregated medium access control (MAC) packet data unit (A-MPDU) frame comprising at least one A-MPDU subframe, the A-MPDU frame having a first length, determine whether an additional A-MPDU subframe having a second length may be added to the A-MPDU frame based at least in part on the first length, the second length, and the target transmission duration, and include one or more padding subframes in the A-MPDU frame based at least in part on a comparison between the first length and the target transmission duration. The user terminal further comprises a transmitter configured to transmit the generated PSDU over the target transmission duration.

Another aspect of the disclosure provides a user terminal for wireless communication.

The user terminal comprises means for receiving a trigger frame from an access point indicating a target transmission duration for transmission of a physical layer (PHY) service data unit (PSDU) to the access point. The user terminal further comprises means for generating an aggregated medium access control (MAC) packet data unit (A-MPDU) frame comprising at least one A-MPDU subframe, the A-MPDU frame having a first length. The user terminal further comprises means for determining whether an additional A-MPDU subframe having a second length may be added to the A-MPDU frame based at least in part on the first length, the second length, and the target transmission duration. The user terminal further comprises means for including one or more padding subframes in the A-MPDU frame based at least in part on a comparison between the first length and the target transmission duration. The user terminal further comprises means for generating the PSDU, the PSDU including the A-MPDU frame. The user terminal further comprises means for transmitting the generated PSDU over the target transmission duration.

Another aspect of the disclosure provides a non-transitory computer readable medium comprising instructions that, when executed, perform a method of communication. The method comprises receiving, at a user terminal, a trigger frame from an access point indicating a target transmission duration for transmission of a physical layer (PHY) service data unit (PSDU) to the access point. The method further comprises generating an aggregated medium access control (MAC) packet data unit (A-MPDU) frame comprising at least one A-MPDU subframe, the A-MPDU frame having a first length. The method further comprises determining whether an additional A-MPDU subframe having a second length may be added to the A-MPDU frame based at least in part on the first length, the second length, and the target transmission duration. The method further comprises including one or more padding subframes in the A-MPDU frame based at least in part on a comparison between the first length and the target transmission duration. The method further comprises generating the PSDU, the PSDU including the A-MPDU frame. The method further comprises transmitting the generated PSDU from the user terminal over the target transmission duration.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Figure 1:
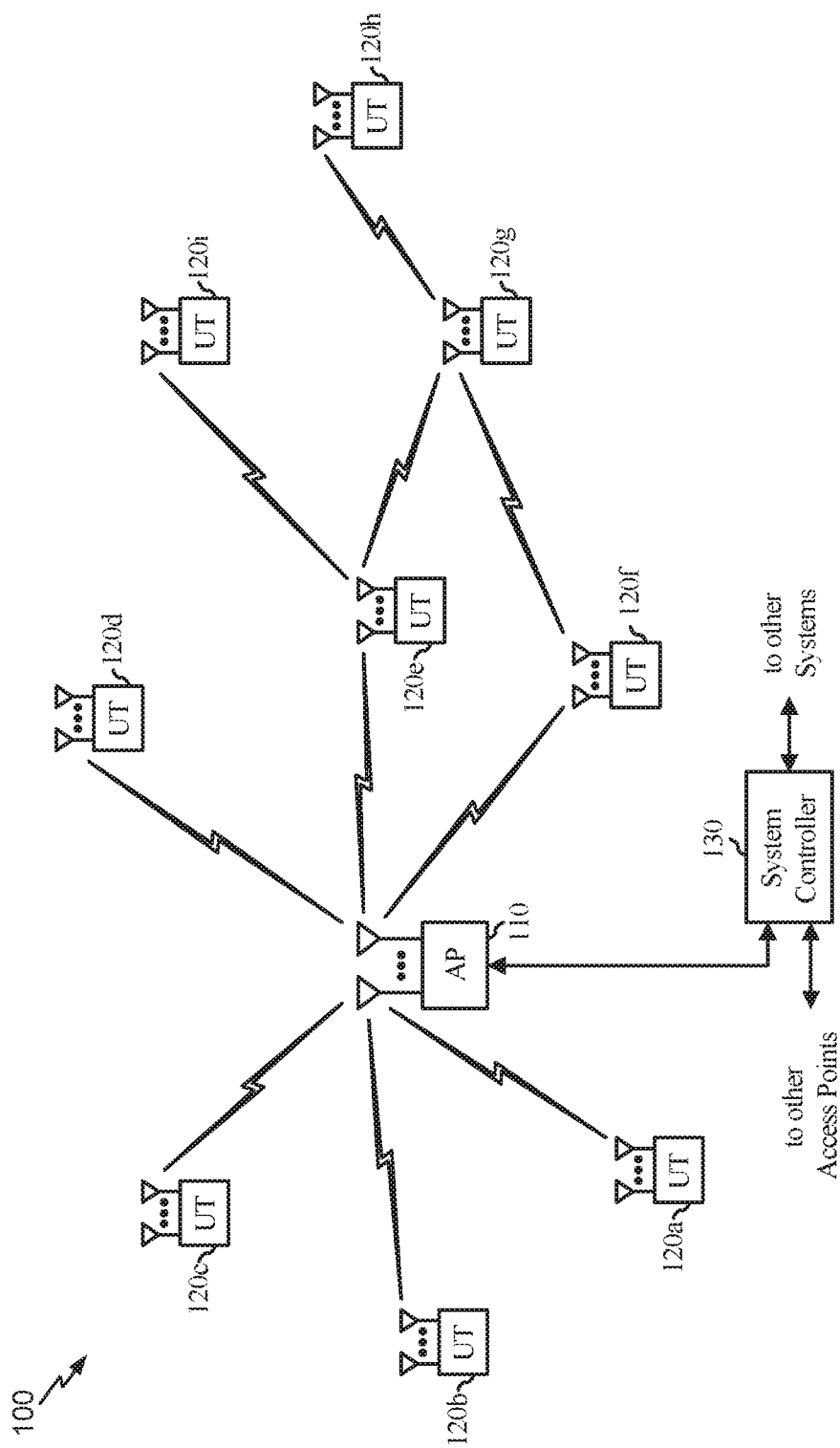
FIG. 1 illustrates a multiple-access multiple-input multiple-output system with access points and user terminals.

Various aspects of the novel systems, apparatuses, and methods are described more fully hereinafter with reference to the accompanying drawings. The teachings disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

Wireless network technologies may include various types of wireless local area networks (WLANs). A WLAN may be used to interconnect nearby devices together, employing widely used networking protocols. The various aspects described herein may apply to any communication standard, such as Wi-Fi or, more generally, any member of the IEEE 802.11 family of wireless protocols.

In some aspects, wireless signals may be transmitted according to a high-efficiency 802.11 protocol using orthogonal frequency-division multiplexing (OFDM), direct-sequence spread spectrum (DSSS) communications, a combination of OFDM and DSSS communications, or other schemes. Implementations of the high-efficiency 802.11 protocol may be used for Internet access, sensors, metering, smart grid networks, or other wireless applications. Advantageously, aspects of certain devices implementing this particular wireless protocol may consume less power than devices implementing other wireless protocols, may be used to transmit wireless signals across short distances, and/or may be able to transmit signals less likely to be blocked by objects, such as humans.

In some implementations, a WLAN includes various devices which are the components that access the wireless network. For example, there may be two types of devices: access points ("APs") and clients (also referred to as stations, or "STAs"). In general, an AP serves as a hub or base station for the WLAN and an STA serves as a user of the WLAN. For example, a STA may be a laptop computer, a personal digital assistant (PDA), a mobile phone, etc. In an example, an STA connects to an AP via a Wi-Fi (e.g., IEEE 802.11 protocol such as 802.11ah) compliant wireless link to obtain general connectivity to the Internet or to other wide area networks. In some implementations an STA may also be used as an AP.

The techniques described herein may be used for various broadband wireless communication systems, including communication systems that are based on an orthogonal multiplexing scheme. Examples of such communication systems include Spatial Division Multiple Access (SDMA), Time Division Multiple Access (TDMA), Orthogonal Frequency Division Multiple Access (01-DMA) systems, Single-Carrier Frequency Division Multiple Access (SC-1-DMA) systems, and so forth. An SDMA system may utilize sufficiently different directions to simultaneously transmit data belonging to multiple user terminals. A TDMA system may allow multiple user terminals to share the same frequency channel by dividing the transmission signal into different time slots, each time slot being assigned to different user terminal. A TDMA system may implement GSM or some other standards known in the art. An OFDMA system utilizes orthogonal frequency division multiplexing (OFDM), which is a modulation technique that partitions the overall system bandwidth into multiple orthogonal sub-carriers. These sub-carriers may also be called tones, bins, etc. With OFDM, each sub-carrier may be independently modulated with data. An 01-DM system may implement IEEE 802.11 or some other standards known in the art. An SC-FDMA system may utilize interleaved FDMA (IFDMA) to transmit on sub-carriers that are distributed across the system bandwidth, localized FDMA (LFDMA) to transmit on a block of adjacent sub-carriers, or enhanced FDMA (EFDMA) to transmit on multiple blocks of adjacent sub-carriers. In general, modulation symbols are sent in the frequency domain with OFDM and in the time domain with SC-1-DMA. A SC-FDMA system may implement 3GPP-LTE (3rd Generation Partnership Project Long Term Evolution) or other standards.

The teachings herein may be incorporated into (e.g., implemented within or performed by) a variety of wired or wireless apparatuses (e.g., nodes). In some aspects, a wireless node implemented in accordance with the teachings herein may comprise an access point or an access terminal.

An access point ("AP") may comprise, be implemented as, or known as a NodeB, Radio Network Controller ("RNC"), eNodeB, Base Station Controller ("BSC"), Base Transceiver Station ("BTS"), Base Station ("BS"), Transceiver Function ("TF"), Radio Router, Radio Transceiver, Basic Service Set ("BSS"), Extended Service Set ("ESS"), Radio Base Station ("RBS"), or some other terminology.

A station "STA" may also comprise, be implemented as, or known as a user terminal, an access terminal ("AT"), a subscriber station, a subscriber unit, a mobile station, a remote station, a remote terminal, a user agent, a user device, user equipment, or some other terminology. In some implementations an access terminal may comprise a cellular telephone, a cordless telephone, a Session Initiation Protocol ("SIP") phone, a wireless local loop ("WLL") station, a personal digital assistant ("PDA"), a handheld device having wireless connection capability, or some other suitable processing device connected to a wireless modem. Accordingly, one or more aspects taught herein may be incorporated into a phone (e.g., a cellular phone or smartphone), a computer (e.g., a laptop), a portable communication device, a headset, a portable computing device (e.g., a personal data assistant), an entertainment device (e.g., a music or video device, or a satellite radio), a gaming device or system, a global positioning system device, or any other suitable device that is configured to communicate via a wireless medium.

FIG. 1 is a diagram that illustrates a multiple-access multiple-input multiple-output (MIMO) system 100 with access points and user terminals. For simplicity, only one access point 110 is shown in FIG. 1. An access point is generally a fixed station that communicates with the user terminals and may also be referred to as a base station or using some other terminology. A user terminal or STA may be fixed or mobile and may also be referred to as a mobile station or a wireless device, or using some other terminology. The access point 110 may communicate with one or more user terminals 120 at any given moment on the downlink and uplink. The downlink (i.e., forward link) is the communication link from the access point to the user terminals, and the uplink (i.e., reverse link) is the communication link from the user terminals to the access point. A user terminal may also communicate peer-to-peer with another user terminal. A system controller 130 couples to and provides coordination and control for the access points.

While portions of the following disclosure will describe user terminals 120 capable of communicating via Spatial Division Multiple Access (SDMA), for certain aspects, the user terminals 120 may also include some user terminals that do not support SDMA. Thus, for such aspects, the AP 110 may be configured to communicate with both SDMA and non-SDMA user terminals. This approach may conveniently allow older versions of user terminals ("legacy" stations) that do not support SDMA to remain deployed in an enterprise, extending their useful lifetime, while allowing newer SDMA user terminals to be introduced as deemed appropriate.

The system 100 employs multiple transmit and multiple receive antennas for data transmission on the downlink and uplink. The access point 110 is equipped with $N_{ap}$ antennas and represents the multiple-input (MI) for downlink transmissions and the multiple-output (MO) for uplink transmissions. A set of K selected user terminals 120 collectively represents the multiple-output for downlink transmissions and the multiple-input for uplink transmissions. For pure SDMA, it is desired to have $N_{ap} \leq K \leq 1$ if the data symbol streams for the K user terminals are not multiplexed in code, frequency or time by some means. K may be greater than $N_{ap}$ if the data symbol streams can be multiplexed using TDMA technique, different code channels with CDMA, disjoint sets of sub-bands with OFDM, and so on. Each selected user terminal may transmit user-specific data to and/or receive user-specific data from the access point. In general, each selected user terminal may be equipped with one or multiple antennas (i.e., $N_{ut} \geq 1$). The K selected user terminals can have the same number of antennas, or one or more user terminals may have a different number of antennas.

The SDMA system 100 may be a time division duplex (TDD) system or a frequency division duplex (FDD) system. For a TDD system, the downlink and uplink share the same frequency band. For an FDD system, the downlink and uplink use different frequency bands. The MIMO system 100 may also utilize a single carrier or multiple carriers for transmission. Each user terminal may be equipped with a single antenna (e.g., in order to keep costs down) or multiple antennas (e.g., where the additional cost can be supported). The system 100 may also be a TDMA system if the user terminals 120 share the same frequency channel by dividing transmission/reception into different time slots, where each time slot may be assigned to a different user terminal 120.

Figure 2:
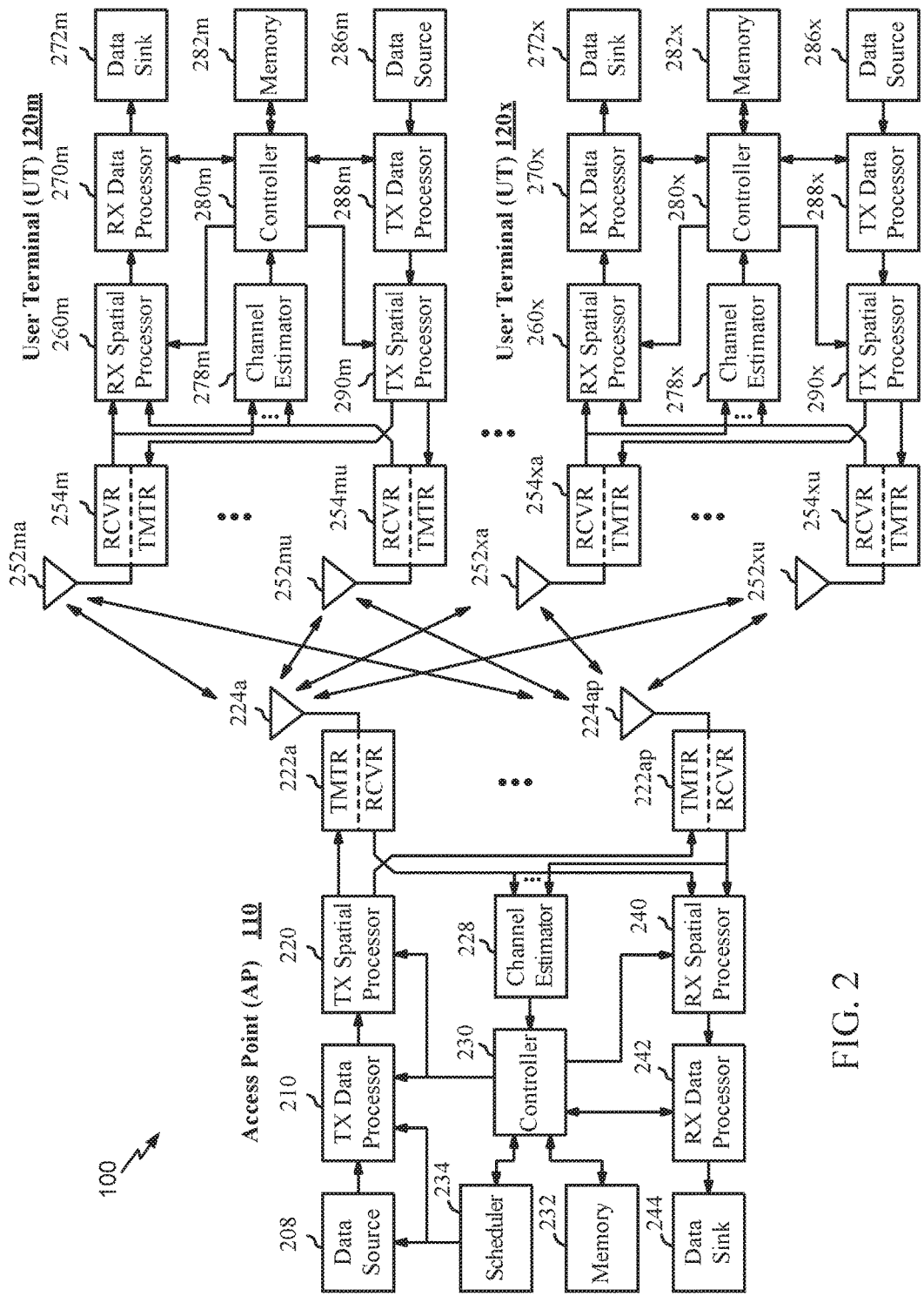
FIG. 2 illustrates a block diagram of the access point 110 and two user terminals 120*m* and 120*x* in a multiple-input multiple-output system.

FIG. 2 illustrates a block diagram of the access point 110 and two user terminals 120m and 120x in MIMO system 100. The access point 110 is equipped with $N_t$ antennas 224a through 224ap. The user terminal 120m is equipped with $N_{ut,m}$ antennas 252ma through $252_{mu}$, and the user terminal 120x is equipped with $N_{ut,x}$ antennas $252_{xa}$ through $252_{xu}$. The access point 110 is a transmitting entity for the downlink and a receiving entity for the uplink. The user terminal 120 is a transmitting entity for the uplink and a receiving entity for the downlink. As used herein, a "transmitting entity" is an independently operated apparatus or device capable of transmitting data via a wireless channel, and a "receiving entity" is an independently operated apparatus or device capable of receiving data via a wireless channel. In the following description, the subscript "dn" denotes the downlink, the subscript "up" denotes the uplink, $N_{up}$ user terminals are selected for simultaneous transmission on the uplink, and $N_{dn}$ user terminals are selected for simultaneous transmission on the downlink. $N_{up}$ may or may not be equal to $N_{dn}$, and $N_{up}$ and $N_{dn}$ may be static values or may change for each scheduling interval. Beam-steering or some other spatial processing technique may be used at the access point 110 and/or the user terminal 120.

On the uplink, at each user terminal 120 selected for uplink transmission, a TX data processor 288 receives traffic data from a data source 286 and control data from a controller 280. The TX data processor 288 processes (e.g., encodes, interleaves, and modulates) the traffic data for the user terminal based on the coding and modulation schemes associated with the rate selected for the user terminal and provides a data symbol stream. A TX spatial processor 290 performs spatial processing on the data symbol stream and provides $N_{ut,m}$ transmit symbol streams for the $N_{ut,m}$ antennas. Each transmitter unit ("TMTR") 254 receives and processes (e.g., converts to analog, amplifies, filters, and frequency upconverts) a respective transmit symbol stream to generate an uplink signal. $N_{ut,m}$ transmitter units 254 provide $N_{ut,m}$ uplink signals for transmission from $N_{ut,m}$ antennas 252, for example to transmit to the access point 110.

$N_{up}$ user terminals may be scheduled for simultaneous transmission on the uplink. Each of these user terminals may perform spatial processing on its respective data symbol stream and transmit its respective set of transmit symbol streams on the uplink to the access point 110.

At the access point 110, $N_{up}$ antennas 224a through $224_{ap}$ receive the uplink signals from all $N_{up}$ user terminals transmitting on the uplink. Each antenna 224 provides a received signal to a respective receiver unit ("RCVR") 222. Each receiver unit 222 performs processing complementary to that performed by transmitter unit 254 and provides a received symbol stream. An RX spatial processor 240 performs receiver spatial processing on the $N_{up}$ received symbol streams from $N_{up}$ receiver units 222 and provides $N_{up}$ recovered uplink data symbol streams. The receiver spatial processing may be performed in accordance with the channel correlation matrix inversion (CCMI), minimum mean square error (MMSE), soft interference cancellation (SIC), or some other technique. Each recovered uplink data symbol stream is an estimate of a data symbol stream transmitted by a respective user terminal. An RX data processor 242 processes (e.g., demodulates, deinterleaves, and decodes) each recovered uplink data symbol stream in accordance with the rate used for that stream to obtain decoded data. The decoded data for each user terminal may be provided to a data sink 244 for storage and/or a controller 230 for further processing.

On the downlink, at the access point 110, a TX data processor 210 receives traffic data from a data source 208 for $N_{dn}$ user terminals scheduled for downlink transmission, control data from a controller 230, and possibly other data from a scheduler 234. The various types of data may be sent on different transport channels. TX data processor 210 processes (e.g., encodes, interleaves, and modulates) the traffic data for each user terminal based on the rate selected for that user terminal. The TX data processor 210 provides $N_{dn}$ downlink data symbol streams for the $N_{dn}$ user terminals. A TX spatial processor 220 performs spatial processing (such as a precoding or beamforming) on the $N_{dn}$ downlink data symbol streams, and provides $N_{up}$ transmit symbol streams for the $N_{up}$ antennas. Each transmitter unit 222 receives and processes a respective transmit symbol stream to generate a downlink signal. $N_{up}$ transmitter units 222 may provide $N_{up}$ downlink signals for transmission from $N_{up}$ antennas 224, for example to transmit to the user terminals 120.

At each user terminal 120, $N_{ut,m}$ antennas 252 receive the $N_{up}$ downlink signals from the access point 110. Each receiver unit 254 processes a received signal from an associated antenna 252 and provides a received symbol stream. An RX spatial processor 260 performs receiver spatial processing on $N_{ut,m}$ received symbol streams from $N_{ut,m}$ receiver units 254 and provides a recovered downlink data symbol stream for the user terminal 120. The receiver spatial processing may be performed in accordance with the CCMI, MMSE, or some other technique. An RX data processor 270 processes (e.g., demodulates, deinterleaves and decodes) the recovered downlink data symbol stream to obtain decoded data for the user terminal.

At each user terminal 120, a channel estimator 278 estimates the downlink channel response and provides downlink channel estimates, which may include channel gain estimates, SNR estimates, noise variance and so on. Similarly, a channel estimator 228 estimates the uplink channel response and provides uplink channel estimates. Controller 280 for each user terminal typically derives the spatial filter matrix for the user terminal based on the downlink channel response matrix $H_{dn,m}$ for that user terminal. Controller 230 derives the spatial filter matrix for the access point based on the effective uplink channel response matrix $H_{up,eff}$. The controller 280 for each user terminal may send feedback information (e.g., the downlink and/or uplink eigenvectors, eigenvalues, SNR estimates, and so on) to the access point 110. The controllers 230 and 280 may also control the operation of various processing units at the access point 110 and user terminal 120, respectively.

Figure 3:
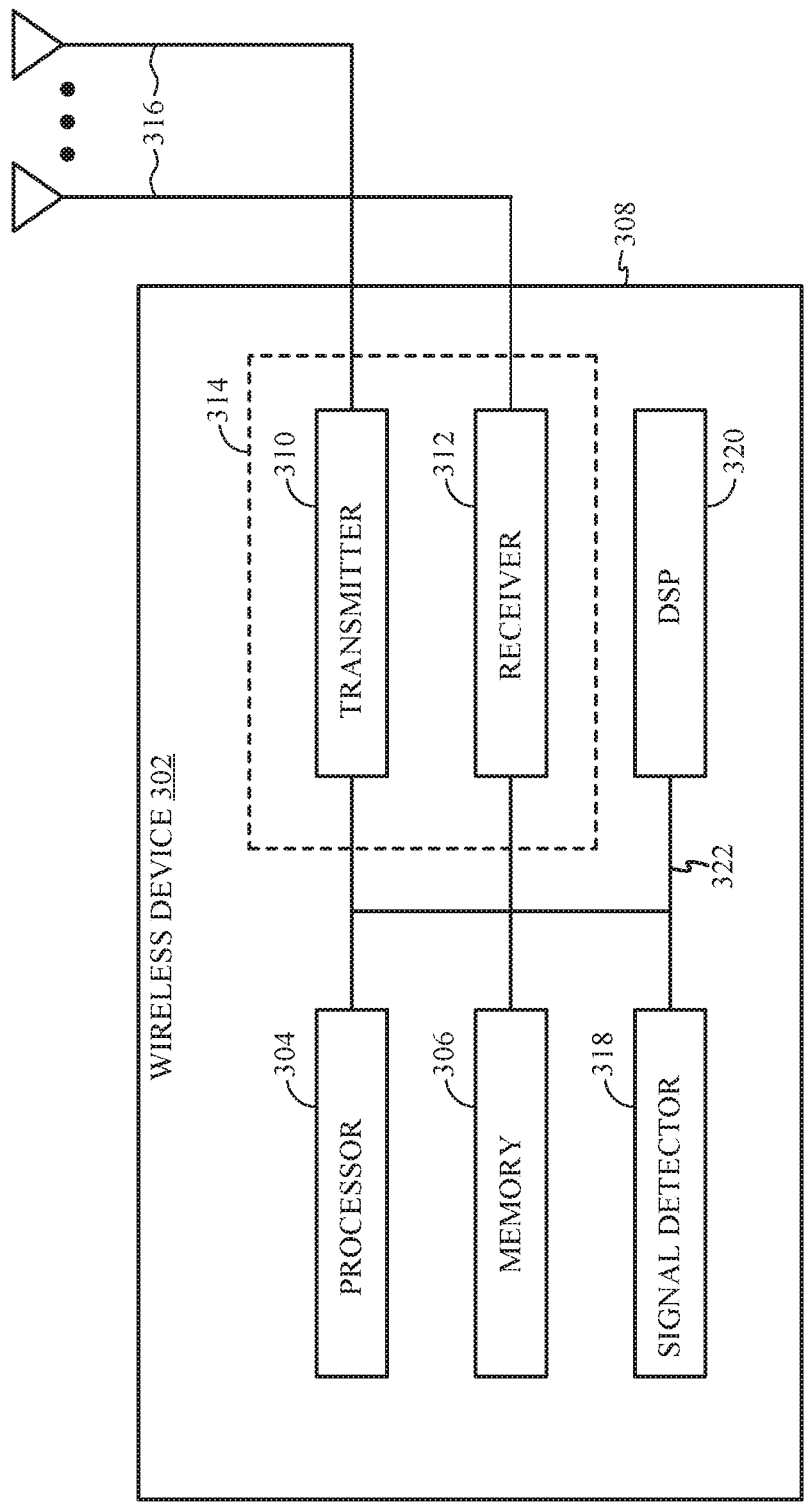
FIG. 3 illustrates various components that may be utilized in a wireless device that may be employed within a wireless communication system.

FIG. 3 illustrates various components that may be utilized in a wireless device 302 that may be employed within the wireless communication system 100. The wireless device 302 is an example of a device that may be configured to implement the various methods described herein. The wireless device 302 may implement an access point 110 or a user terminal 120.

The wireless device 302 may include a processor 304 which controls operation of the wireless device 302. The processor 304 may also be referred to as a central processing unit (CPU). Memory 306, which may include both read-only memory (ROM) and random access memory (RAM), provides instructions and data to the processor 304. A portion of the memory 306 may also include non-volatile random access memory (NVRAM). The processor 304 may perform logical and arithmetic operations based on program instructions stored within the memory 306. The instructions in the memory 306 may be executable to implement the methods described herein.

The processor 304 may comprise or be a component of a processing system implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system may also include machine-readable media for storing software.

Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein.

The wireless device 302 may also include a housing 308 that may include a transmitter 310 and a receiver 312 to allow transmission and reception of data between the wireless device 302 and a remote location. The transmitter 310 and receiver 312 may be combined into a transceiver 314. A single or a plurality of transceiver antennas 316 may be attached to the housing 308 and electrically coupled to the transceiver 314. The wireless device 302 may also include (not shown) multiple transmitters, multiple receivers, and multiple transceivers.

The wireless device 302 may also include a signal detector 318 that may be used in an effort to detect and quantify the level of signals received by the transceiver 314. The signal detector 318 may detect such signals as total energy, energy per subcarrier per symbol, power spectral density and other signals. The wireless device 302 may also include a digital signal processor (DSP) 320 for use in processing signals.

The various components of the wireless device 302 may be coupled together by a bus system 322, which may include a power bus, a control signal bus, and a status signal bus in addition to a data bus.

Certain aspects of the present disclosure support transmitting an uplink (UL) signal from multiple UTs to an AP. In some embodiments, the UL signal may be transmitted in a multi-user MIMO (MU-MIMO) system. Alternatively, the UL signal may be transmitted in a multi-user FDMA (MU-1-DMA) or similar FDMA system. Specifically, FIGS. 4-8 illustrate uplink MU-MIMO (UL-MU-MIMO) transmissions 410A and 410B that would apply equally to UL-OFDMA transmissions. In these embodiments, UL-MU-MIMO or UL-O1-DMA transmissions can be sent simultaneously from multiple STAs to an AP and may create efficiencies in wireless communication.

An increasing number of wireless and mobile devices put increasing stress on bandwidth requirements that are demanded for wireless communications systems. With limited communication resources, it is desirable to reduce the amount of traffic passing between the AP and the multiple STAs. For example, when multiple terminals send uplink communications to the access point, it is desirable to minimize the amount of traffic to complete the uplink of all transmissions. Thus, embodiments described herein support utilizing communication exchanges, scheduling and certain frames for increasing throughput of uplink transmissions to the AP.

Figure 4:
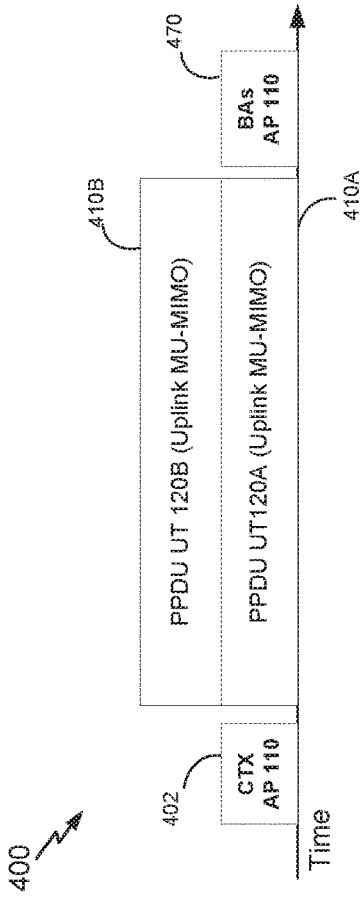
FIG. 4 shows a time diagram of an example frame exchange of an uplink multi-user multiple-input multiple-output communication.

FIG. 4 is a time sequence diagram 400 showing an example of an UL-MU-MIMO protocol 400 that may be used for UL communications. As shown in FIG. 4, in conjunction with FIG. 1, the AP 110 may transmit a clear to transmit (CTX) message 402 to the user terminals 120 indicating which user terminals 120 may participate in the UL-MU-MIMO scheme, such that a particular UT 120 knows to start an UL-MU-MIMO transmission. In some embodiments, the CTX message 402 may be transmitted in a payload portion of a physical layer convergence protocol (PLCP) protocol data units (PPDUs). An example of a CTX frame structure is described more fully below with reference to FIG. 10.

Once a user terminal 120 receives a CTX message 402 from the AP 110 where the user terminal is listed, the user terminal 120 may transmit the UL-MU-MIMO transmission 410. In FIG. 4, STA 120A and STA 120B transmit UL-MU-MIMO transmissions 410A and 410B, respectively, containing physical layer convergence protocol (PLCP) protocol data units (PPDUs). Upon receiving the UL-MU-MIMO transmissions 410A and 410B, the AP 110 may transmit block acknowledgments (BAs) 470 to the user terminals 120A and 120B.

Not all APs 110 or user terminals 120 may support UL-MU-MIMO or UL-01-DMA operation. A capability indication from a user terminal 120 may be indicated in a high efficiency wireless (HEW) capability element that is included in an association request or probe request and may include a bit indicating capability, the maximum number of spatial streams a user terminal 120 can use in a UL-MU-MIMO transmission, the frequencies a user terminal 120 can use in a UL-OFDMA transmission, the minimum and maximum power and granularity in the power backoff, and the minimum and maximum time adjustment a user terminal 120 can perform.

A capability indication from an AP 110 may be indicated in a HEW capability element that is included in an association response, beacon or probe response and may include a bit indicating capability, the maximum number of spatial streams a single user terminal 120 can use in a UL-MU-MIMO transmission, the frequencies a single user terminal 120 can use in a UL-OFDMA transmission, the required power control granularity, and the required minimum and maximum time adjustment a user terminal 120 should be able to perform.

In one embodiment, capable user terminals 120 may request to a capable AP to be part of the UL-MU-MIMO (or UL-01-DMA) protocol. The request may be included in a management frame, a request to send (RTS) message, a quality of service (QoS) frame, a power save (PS) poll, or an RTX frame. In one aspect, an AP 110 may respond by granting the user terminal 120 the use of the UL-MU-MIMO feature or the AP 110 may deny the user terminal's request. The AP 110 may grant the use of the UL-MU-MIMO and the user terminal 120 may expect a CTX message 402 at a variety of times. Additionally, once a user terminal 120 is enabled to operate the UL-MU-MIMO feature, the user terminal 120 may be subject to following a certain operation mode. The user terminal 120 and the AP 110 may support multiple operation modes and the AP 110 may indicate to the user terminal 120 which mode to use in a HEW capability element, a management frame, or in an operation element. In one aspect, a user terminal 120 may change the operation mode and parameters dynamically during operation by sending a different operating element to the AP 110. In another aspect the AP 110 may switch the operation mode dynamically during operation by sending an updated operating element or a management frame to the user terminal 120, or by sending the updated operating element or the updated management frame in a beacon. In another aspect, the operation mode may be determined by the AP 110 in the setup phase and may be determined per user terminal 120 or for a group of user terminals 120. In another aspect the operation mode may be specified per traffic identifier (TID).

In some operation modes of UL-MU-MIMO transmissions, a user terminal 120 may receive a CTX message from an AP 110 and immediately send a response to the AP 110. The response may be in the form of a clear to send (CTS) message or another type of message. The requirement to send the CTS message may be indicated in the CTX message or the requirement may be indicated in the setup phase of the communication between the AP 110 and the user terminal 120.

Figure 5:
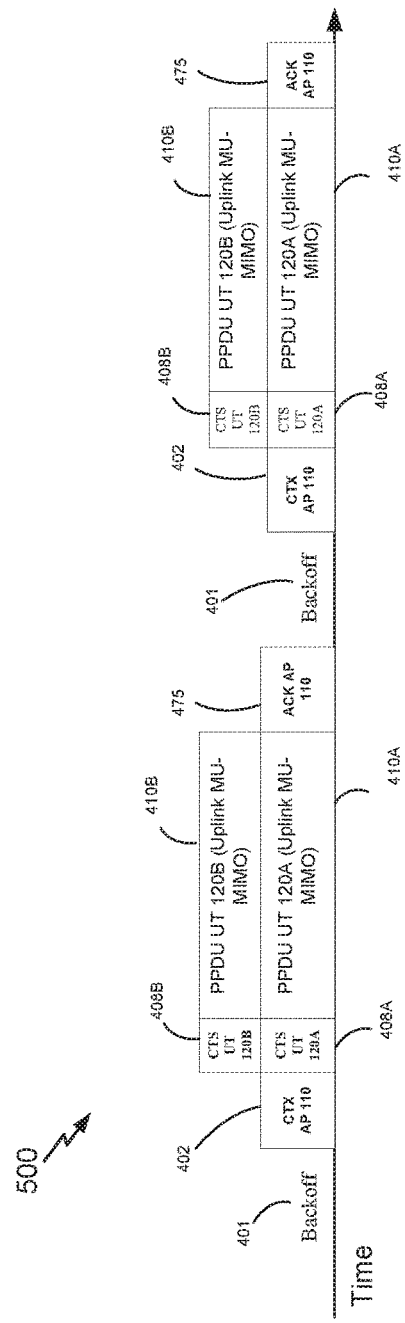
FIG. 5 shows a time sequence diagram of another example frame exchange of an uplink multi-user multiple-input multiple-output communication.

FIG. 5 is a time sequence diagram 500 that, in conjunction with FIG. 1, shows an example of an operation mode of UL-MU-MIMO transmissions between an AP 110 and user terminals 120A and 120B. As shown in FIG. 5, UT 120A may transmit a CTS message 408A and UT 120B may transmit a CTS message 408B in response to receiving the CTX message 402 from the AP 110. The modulation and coding scheme (MCS) of the CTS message 408A and the CTS message 408B may be based on the MCS of the CTX message 402. In this embodiment, the CTS message 408A and the CTS message 408B contain the same amount of bits and the same scrambling sequence so that they may be transmitted to the AP 110 at the same time. A duration field of the CTS messages 408A and 408B may be based on a duration field in the CTX by removing the time for the CTX PPDU. The user terminal 120A may send an UL-MU-MIMO transmission 410A to the AP 110 according to the CTX message 402 and the user terminal 120B may also send an UL-MU-MIMO transmission 410B to the AP 110 according to the CTX message 402. The AP 110 may then send an acknowledgment (ACK) message 475 to the user terminals 120A and 120B. In some aspects, the ACK message 475 may include serial ACK messages sent to each user terminal 120 or the ACK message 475 may include BAs. In some aspects the ACKs 475 may be polled. The embodiment of FIG. 5 may improve transmission efficiency by providing concurrent transmission of CTS messages 408 from multiple user terminals 120 to an AP 110, compared to sequential transmission, thereby saving time and reducing the possibility of interference.

Figure 6:
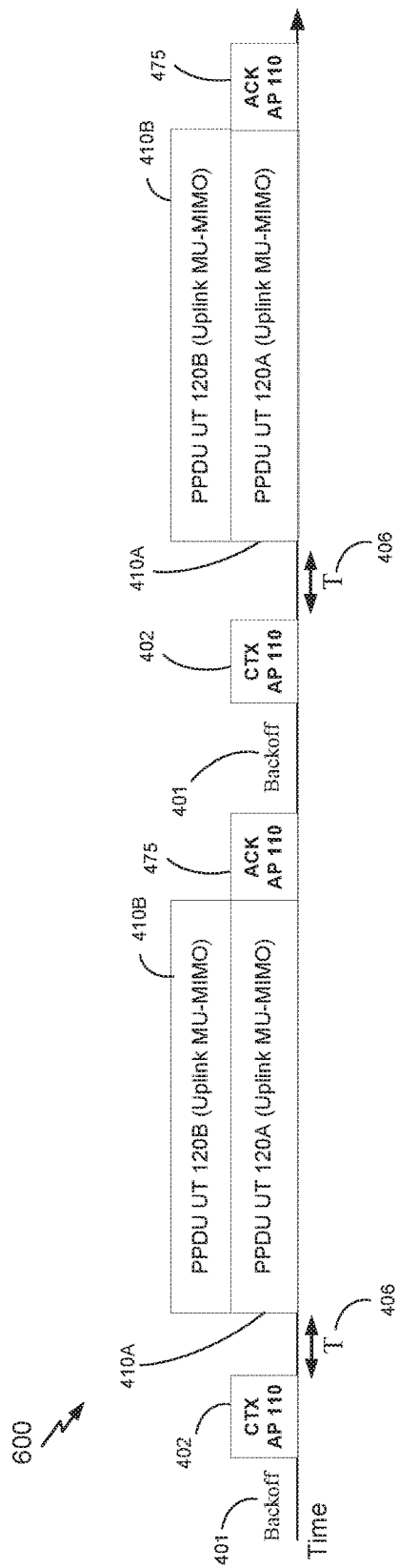
FIG. 6 shows a time sequence diagram of another example frame exchange of an uplink multi-user multiple-input multiple-output communication.

FIG. 6 is a time sequence diagram 600 that, in conjunction with FIG. 1, shows an example of an operation mode of UL-MU-MIMO transmissions. In this embodiment, user terminals 120A and 120B may receive a CTX message 402 from an AP 110. The CTX message 402 may indicate a time (T) 406 after the end of the PPDU carrying the CTX message 402 for the user terminals 120A and 120B to transmit UL-MU-MIMO transmissions. The T 406 may be a short interframe space (SIFS), a point interframe space (PIFS), or another time. The T may include time offsets as indicated by the AP 110 in the CTX message 402 or via a management frame. The SIFS and PIFS time may be fixed in a standard or may be indicated by the AP 110 in the CTX message 402 or in a management frame. The T 406 may improve synchronization between the AP 110 and the user terminals 120A and 120B and it may allow the user terminals 120A and 120B sufficient time to process the CTX message 402, or other messages, before sending their UL-MU-MIMO transmissions.

In some circumstances, a user terminal 120 may have data to upload to the AP 110 but the user terminal 120 may not have received a CTX message 402 or another message indicating that the user terminal 120 may start an UL-MU-MIMO transmission. In one operation mode, the user terminals 120 may not transmit data outside of an UL-MU-MIMO transmission opportunity (TXOP) (e.g., after CTX message). In another operation mode, user terminals 120 may transmit frames to the AP 110 to initialize a UL-MU-MIMO transmission and may then transmit during the UL-MU-MIMO TXOP, if for example, they are instructed to do so in a CTX message. In one embodiment, the frame to initialize a UL-MU-MIMO transmission may be a request to transmit (RTX), a frame specifically designed for this purpose (an example of a RTX frame structure is described more fully below with reference to FIG. 9). In some operation modes, the RTX frames may be the only frame type a user terminal 120 may use to initiate a UL-MU-MIMO TXOP. In some embodiments, the user terminal 120 may not transmit outside of an UL-MU-MIMO TXOP other than by sending an RTX.

In other embodiments, a frame sent by a user terminal 120 to initialize an UL-MU-MIMO transmission may be any frame which indicates to an AP 110 that a user terminal 120 has data to send. The AP 110 and the user terminal 120 may determine during setup that such frames may indicate an UL-MU-MIMO TXOP request. For example, the following may be used to indicate that a user terminal 120 has data to send and is requesting an UL-MU-MIMO TXOP: an RTS, a data frame or QoS Null set to indicate more data, or a PS poll. For example, the data frame or QoS null frame may have bits 8-15 of the QoS control frame set to indicate more data. In one embodiment, the user terminal 120 may not transmit outside an UL-MU-MIMO TXOP other than by sending frames to trigger this TXOP, where this frame may be an RTS, PS poll, or QOS null. In another embodiment, the user terminal 120 may send single user uplink data as usual, and may indicate a request for an UL-MU-MIMO TXOP by setting bits in the QoS control frame of its data packet.

Figure 7:
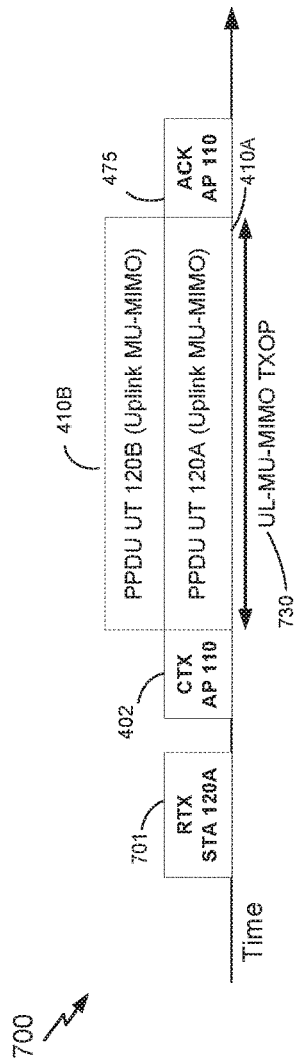
FIG. 7 shows a time sequence diagram of another example frame exchange of an uplink multi-user multiple-input multiple-output communication.

FIG. 7 is a time sequence diagram 700 showing, in conjunction with FIG. 1, an example of UL-MU-MIMO communications including a user terminal 120A sending an RTX message 701 to the AP 110 to request and initialize an UL-MU-MIMO transmission. In this embodiment, the RTX message 701 sent to the AP 110 by the user terminal 120A includes information regarding UL-MU-MIMO transmissions. In other embodiments, an RTX message may be sent by the user terminal 120B. As shown in FIG. 7, the AP 110 may respond to the RTX message 701 with a CTX message 402 granting an UL-MU-MIMO TXOP 730 to the user terminal 120A for sending a UL-MU-MIMO transmission 410A immediately following the CTX message 402. The CTX message 402 may also grant the UL-MU-MIMO TXOP 730 to the user terminal 120B for concurrently sending a UL-MU-MIMO transmission 410B with the UL-MU-MIMO transmission 410A, both transmissions 410A and 410B immediately following the CTX message 402. As described above, the user terminal 120A may send the UL-MU-MIMO transmission 410A for a duration indicated by the AP 110 in the CTX 402 and the user terminal 120B may also send the UL-MU-MIMO transmission 410B for the same duration.

In another aspect, the AP 110 may respond with a CTS that grants a single-user (SU) UL TXOP. In another aspect, the AP 110 may respond with a frame (e.g., ACK or CTX with a special indication) that acknowledges the reception of the RTX 701 but does not grant an immediate UL-MU-MIMO TXOP. In another aspect, the AP 110 may respond with a frame that acknowledges the reception of the RTX 701, does not grant an immediate UL-MU-MIMO TXOP, but grants a delayed UL-MU-MIMO TXOP and may identify the time that the TXOP is granted. In this embodiment, the AP 110 may send a CTX message 402 to start the UL-MU-MIMO at the granted time.

In another aspect, the AP 110 may respond to the RTX 701 with an ACK or other response signal which does not grant the user terminal 120 an UL-MU-MIMO transmission but indicates that the user terminal 120 shall wait for a time (T) before attempting another transmission (e.g., sending another RTX). In this aspect the time (T) may be indicated by the AP 110 in the setup phase or in the response signal. In another aspect an AP 110 and a user terminal 120 may agree on a time which the user terminal 120 may transmit a RTX 701, RTS, PS-poll, or any other request for a UL-MU-MIMO TXOP.

In another operation mode, user terminals 120 may transmit requests for UL-MU-MIMO transmissions 410 in accordance with regular contention protocol. In another aspect, the contention parameters for user terminals 120 using UL-MU-MIMO are set to a different value than for other user terminals that are not using the UL-MU-MIMO feature. In this embodiment, the AP 110 may indicate the value of the contention parameters in a beacon, in an association response or through a management frame. In another aspect, the AP 110 may provide a delay timer that prevents a user terminal 120 from transmitting for a certain amount of time after each successful UL-MU-MIMO TXOP or after each RTX, RTS, PS-poll, or QoS null frame. The timer may be restarted after each successful UL-MU-MIMO TXOP. In one aspect, the AP 110 may indicate the delay timer to user terminals 120 in the setup phase or the delay timer may be different for each user terminal 120. In another aspect, the AP 110 may indicate the delay timer in the CTX message 402 or the delay timer may be dependent on the order of the user terminals 120 in the CTX message 402, and may be different for each terminal.

In another operational mode, the AP 110 may indicate a time interval during which the user terminals 120 are allowed to transmit a UL-MU-MIMO transmission. In one aspect, the AP 110 indicates a time interval to the user terminals 120 during which the user terminals are allowed to send a RTX or RTS or other request to the AP 110 to ask for an UL-MU-MIMO transmission. In this aspect, the user terminals 120 may use regular contention protocol. In another aspect, the user terminals may not initiate a UL-MU-MIMO transmission during the time interval but the AP 110 may send a CTX or other message to the user terminals to initiate the UL-MU-MIMO transmission.

In certain embodiments, a user terminal 120 enabled for UL-MU-MIMO may indicate to an AP 110 that it requests an UL-MU-MIMO TXOP because it has data pending for UL. In one aspect, the user terminal 120 may send a RTS or a PS-poll to request a UL-MU-MIMO TXOP. In another embodiment, the user terminal 120 may send any data frame, including a quality of service (QoS) null data frame, where the bits 8-15 of the QoS control field indicate a non-empty queue. In this embodiment the user terminal 120 may determine during the setup phase which data frames (e.g., RTS, PS-poll, QoS null, etc.) will trigger a UL-MU-MIMO transmission when the bits 8-15 of the QoS control field indicate a non-empty queue. In one embodiment, the RTS, PS-poll, or QoS null frames may include a 1 bit indication allowing or disallowing the AP 110 to respond with a CTX message 402. In another embodiment, the QoS null frame may include TX power information and a per TID queue information. The TX power information and per TID queue information may be inserted in the two bytes of the sequence control and QoS controls fields in a QoS null frame and the modified QoS null frame may be sent to the AP 110 to request a UL-MU-MIMO TXOP. In another embodiment, referring to FIGS. 1 and 7, the user terminal 120 may send a RTX 701 to request a UL-MU-MIMO TXOP.

As described above with reference to FIGS. 4-7, in response to receiving an RTS, RTX, PS-poll or QoS null frame, or other trigger frame as described above, an AP 110 may send a CTX message 402. In one embodiment, after the transmission of the CTX message 402 and the completion of the UL-MU-MIMO transmissions 410A and 410B, the TXOP may return to the user terminals 120A and 120B which may decide on how to use the remaining TXOP. In another embodiment, after the transmission of the CTX message 402 and the completion of the UL-MU-MIMO transmissions 410A and 410B, the TXOP may return to the AP 110 and the AP 110 may use the remaining TXOP for additional UL-MU-MIMO transmissions by sending another CTX message 402 to either UTs 120A and 120B or to other UTs.

Figure 8:
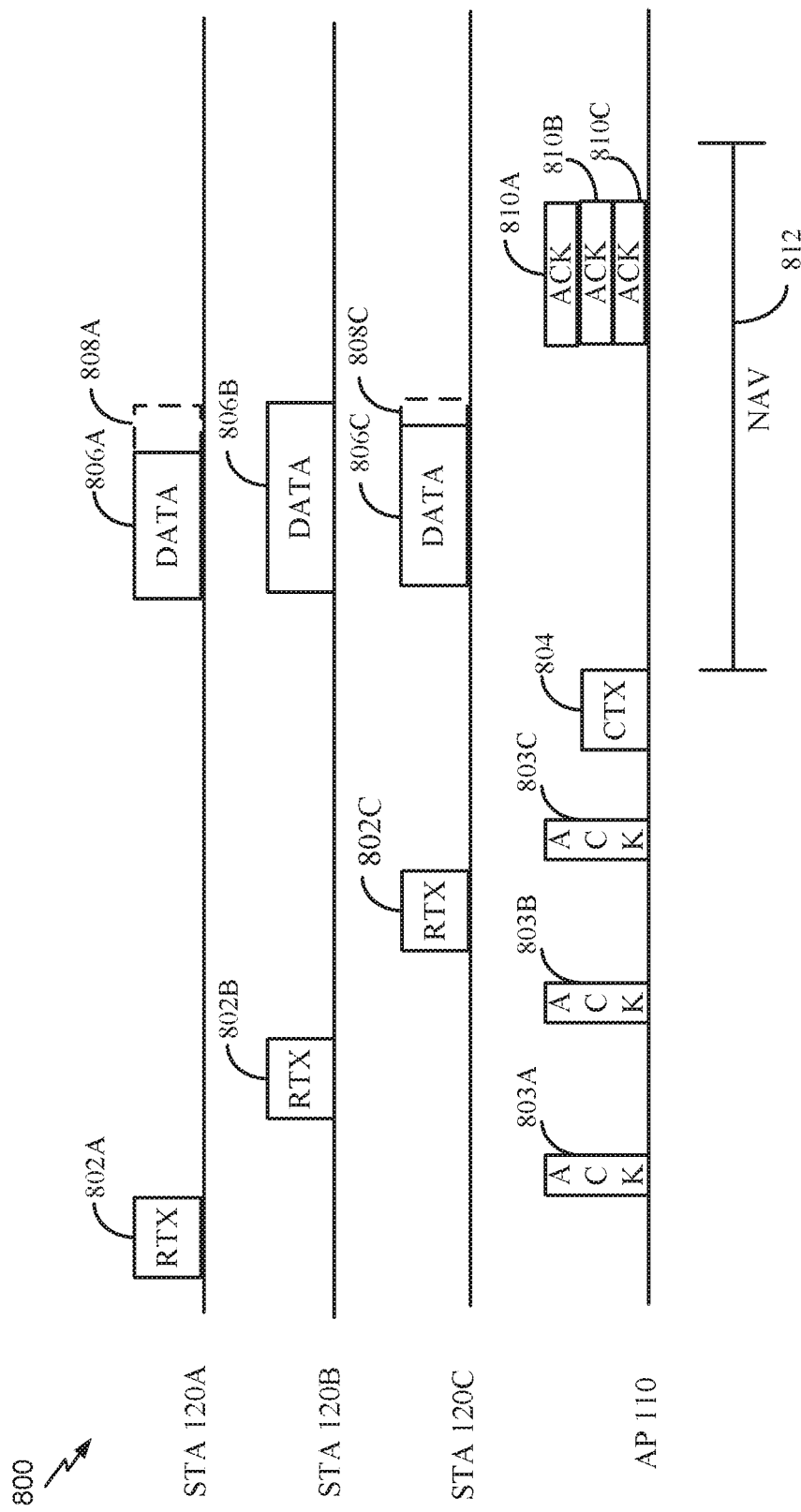
FIG. 8 shows a time sequence diagram of uplink multi-user multiple-input multiple-output communication.

FIG. 8 is a message timing diagram 800 showing multi-user uplink communication.

The message exchange shows communication of wireless messages between an AP 110 and three user terminals 120A-C. The message exchange may indicate that each of the user terminals 120A-C may transmit a request-to-transmit (RTX) message 802A-C to the AP 110. Each of the RTX messages 802A-C may indicate that the transmitting user terminal 120A-C has data available to be transmitted to the AP 110.

After receiving each of RTX messages 802A-C, the AP 110 may respond with a message indicating that the AP 110 has received the each of the RTX messages 802A-C from the user terminals 120A-C. As shown in FIG. 8, the AP 110 may transmit ACK messages 803A-C in response to each RTX messages 802A-C. In some embodiments, the AP 110 may transmit a message (e.g., a CTX message) indicating that each of the RTX messages 802A-C has been received but that the AP 110 has not granted a transmission opportunity for the user terminals 120A-C to uplink data. In FIG. 8, after sending the last ACK message 803C, the AP 110 may transmit a CTX message 804. In some aspects, the CTX message 804 is transmitted to at least the user terminals 120A-C. In some aspects, the CTX message 804 is a broadcast message. The CTX message 804 may indicate which user terminals are granted permission to transmit data to the AP 110 during a transmission opportunity. The CTX message 804 may also indicate a starting time of the transmission opportunity and a duration of the transmission opportunity. For example, the CTX message 804 may indicate that the user terminals 120A-C should set their network allocation vectors to be consistent with NAV 812.

At a time indicated by the CTX message 804, the three user terminals 120A-C transmit data 806A-C to the AP 110. The data 806A-C are transmitted at least partially concurrently during the transmission opportunity. The transmissions of data 806A-C may utilize uplink multi-user multiple input, multiple output transmissions (UL-MU-MIMO) or uplink frequency division multiple access (UL-OFDMA).

In some aspects, user terminals 120A-C may transmit padded data such that the transmissions of each user terminal transmitting during a transmission opportunity are of equal duration or approximately equal duration. In the message exchange of FIG. 8, the user terminal 120A may transmit pad data 808A, the user terminal 120C may not transmit pad data, and the user terminal 120C may transmit pad data 808C. The transmission of pad data ensures that the transmissions from each of the UTs 120A-C complete at approximately the same time. This may provide for a more equalized transmission power over the entire duration of the transmission, thereby optimizing AP 110 receiver efficiencies.

After the AP 110 receives the data transmissions 806A-C from the user terminals 120A-C, the AP 110 may transmit acknowledgment messages 810A-C to each of the user terminals 120A-C. In some aspects, the acknowledgments messages 810A-C may be transmitted at least partially concurrently using either DL-MU-MIMO or DL-1-DMA.

Figure 9:
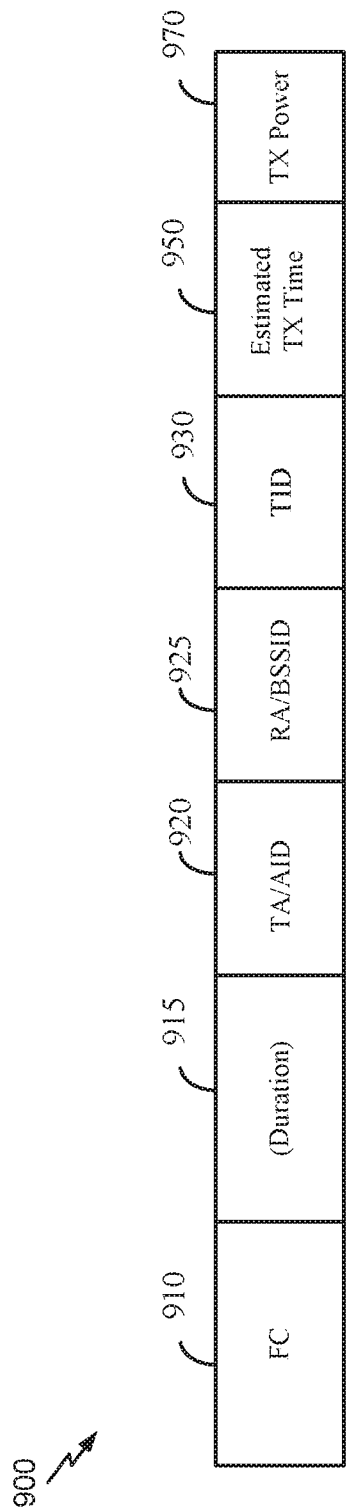
FIG. 9 shows a diagram of a request to transmit frame.

FIG. 9 is a diagram of one embodiment of an RTX frame 900. The RTX frame 900 may include a frame control (FC) field 910, an optional duration field 915, a transmitter address/allocation identifier (TA/AID) field 920, a receiver address/basic service set identifier (RA/BSSID) field 925, a TID field 930, an estimated transmission (TX) time field 950, and a TX power field 970. The FC field 910 may indicate a control subtype or an extension subtype. The duration field 915 may indicate to any receiver of the RTX frame 900 to set the network allocation vector (NAV). In one aspect, the RTX frame 900 may not have a duration field 915. The TA/AID field 920 may indicate a source address, which may be an AID or a full MAC address. The RA/BSSID field 925 may indicate the RA or BSSID. In one aspect, the RTX frame 900 may not contain a RA/BSSID field 925. The TID field 930 may indicate an access category (AC) for which a user terminal has data. The estimated TX time field 950 may indicate a time requested for a UL-TXOP based on an amount of time required for a user terminal 120 to send all the data in its buffer at the current planned MCS. The TX power field 970 may indicate the power at which the RTX frame 900 is being transmitted and may be used by the AP 110 to estimate the link quality and adapt the power backoff indication in a CTX frame.

In some embodiments, before an UL-MU-MIMO communication can take place, an AP 110 may collect information from the user terminals 120 that are participating in the UL-MU-MIMO communication. The AP 110 may optimize the collection of information from the user terminals 120 by scheduling the UL transmissions from the user terminals 120.

Figure 10:
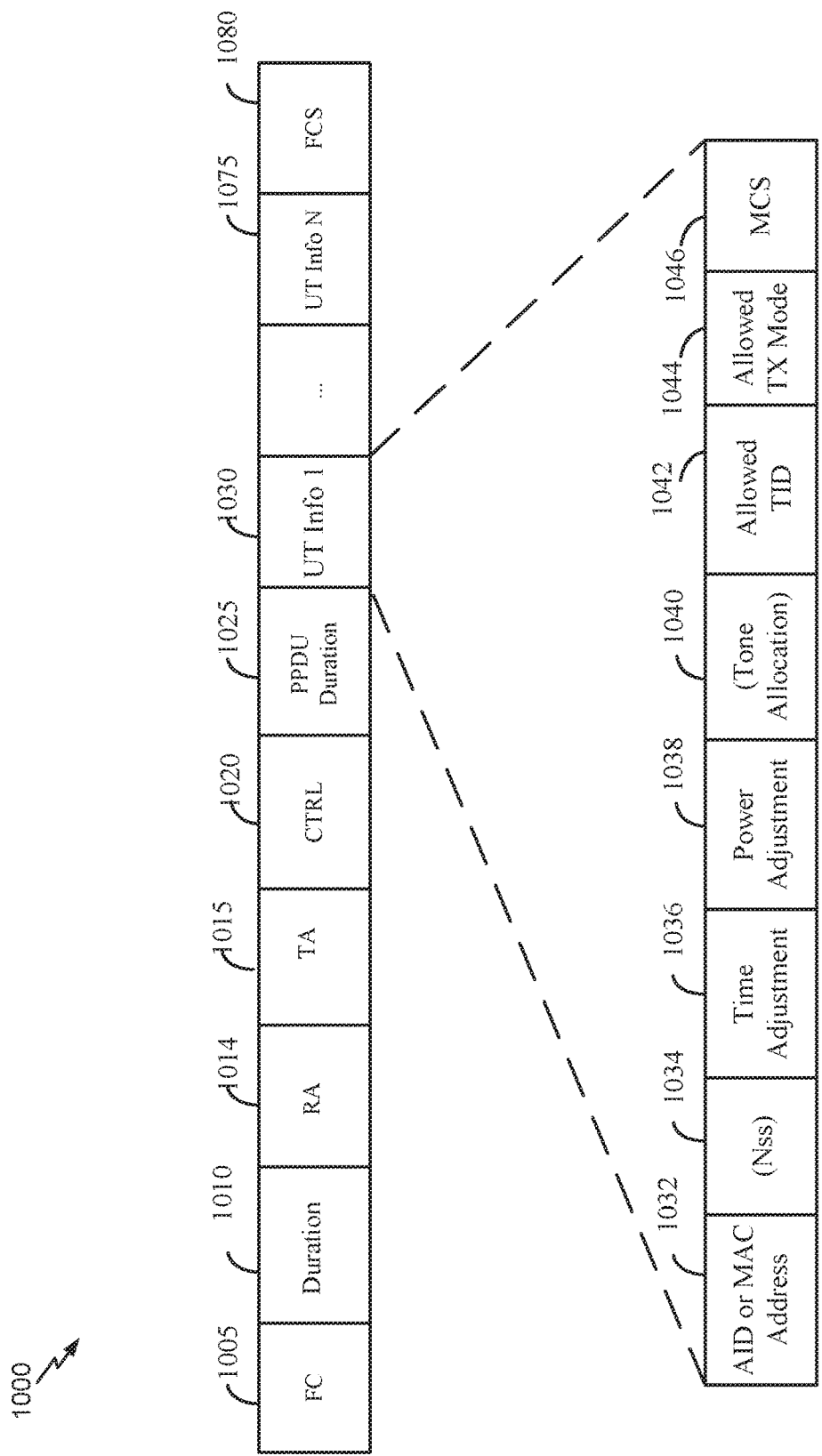
FIG. 10 shows a diagram of a clear to transmit frame.

As discussed above, the CTX message 402 may be used in a variety of communications. FIG. 10 is a diagram of an example of a CTX frame 1000 structure. In this embodiment, the CTX frame 1000 is a control frame that includes a frame control (FC) field 1005, a duration field 1010, a receiver address field 1014, a transmitter address (TA) field 1015, a control (CTRL) field 1020, a PPDU duration field 1025, a UT info field 1030, and a frame check sequence (FCS) field 1080. The FC field 1005 indicates a control subtype or an extension subtype. The duration field 1010 indicates to any receiver of the CTX frame 1000 to set the network allocation vector (NAV). In some embodiments the RA 1014 field identifies a group of UTs through a multicast MAC address. The TA field 1015 indicates the transmitter address or a BSSID. The CTRL field 1020 is a generic field that may include information regarding the format of the remaining portion of the frame (e.g., the number of UT info fields and the presence or absence of any subfields within a UT info field), indications for rate adaptation for the user terminals 120, indication of allowed TID, and indication that a CTS must be sent immediately following the CTX frame 1000. The CTRL field 1020 may also indicate if the CTX frame 1000 is being used for UL-MU-MIMO or for UL FDMA or both, indicating whether a Nss or Tone allocation field is present in the UT Info field 1030. Alternatively, the indication of whether the CTX is for UL-MU-MIMO or for UL FDMA can be based on the value of the subtype. Note that UL-MU-MIMO and UL FDMA operations can be jointly performed by specifying to a UT both the spatial streams to be used and the channel to be used, in which case both fields are present in the CTX; in this case, the Nss indication is referred to a specific tone allocation. The PPDU duration 1025 field indicates the duration of the following UL-MU-MIMO PPDU that the user terminals 120 are allowed to send. The AP 110 may determine the duration of the following Mu-MIMO PPDU that the user terminals 120 are allowed to send based on estimated TX time fields received in at least one RTX message from the user terminals 120. The UT Info 1030 field contains information regarding a particular UT and may include a per-UT (per user terminal 120) set of information (see UT Info 1 1030 and UT Info N 1075). The UT Info 1030 field may include an AID or MAC address field 1032 which identifies a UT, a number of spatial streams field (Nss) 1034 field which indicates the number of spatial streams a UT may use (in an UL-MU-MIMO system), a Time Adjustment 1036 field which indicates a time that a UT should adjust its transmission compared to the reception of a trigger frame (the CTX in this case), a Power Adjustment 1038 field which indicates a power backoff a UT should take from a declared transmit power, a Tone Allocation 1040 field which indicates the tones or frequencies a UT may use (in a UL-OFDMA system), an Allowed TID 1042 field which indicates the allowable TID, an Allowed TX Mode 1044 field which indicates the allowed TX modes, and a MCS 1046 field which indicates the MCS the UT should use. A user terminal 120 receiving a CTX with a Allowed TID 1042 indication may be allowed to transmit data only of that TID, data of the same or higher TID, data of the same or lower TID, any data, or only data of that TID first, then if no data is available, data of other TIDs. The FCS 1080 field indicates the carries an FCS value used for error detection of the CTX frame 1000.

Figure 11:
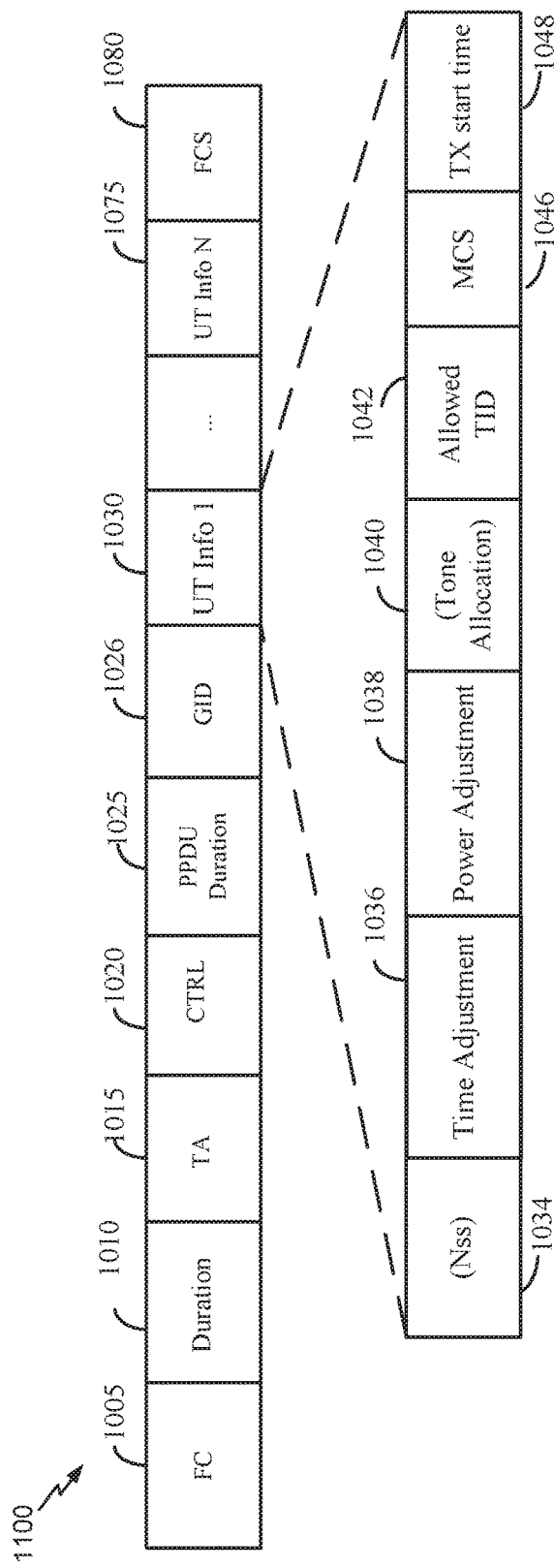
FIG. 11 shows a diagram of another embodiment of a clear to transmit frame.
Figure 12:
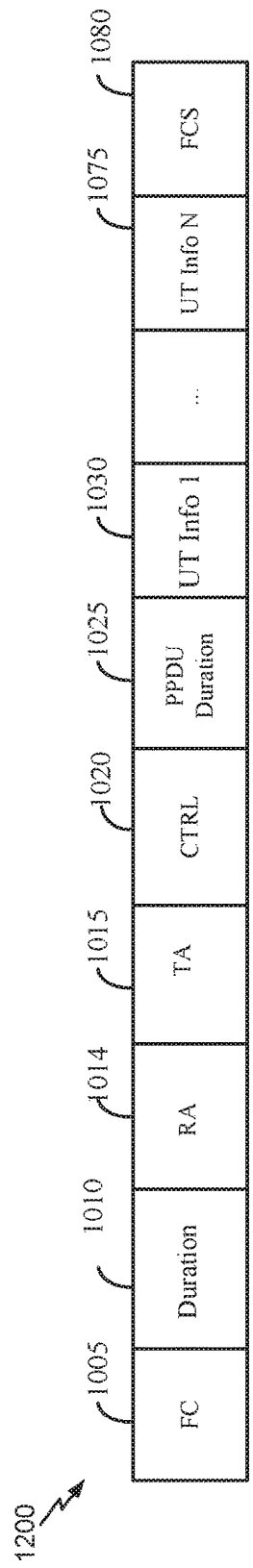
FIG. 12 shows a diagram of another embodiment of a clear to transmit frame.

FIG. 11 is a diagram of another example of a CTX frame 1100 structure. In this embodiment and in conjunction with FIG. 10, the UT Info 1030 field does not contain the AID or MAC Address 1032 field and instead the CTX frame 1000 includes a group identifier (GID) 1026 field which identifies the UTs by a group identifier rather than an individual identifier. FIG. 12 is a diagram of another example of a CTX frame 1200 structure. In this embodiment and in conjunction with FIG. 11, the GID 1026 field is replaced with a RA 1014 field which identifies a group of UTs through a multicast MAC address.

Figure 13:
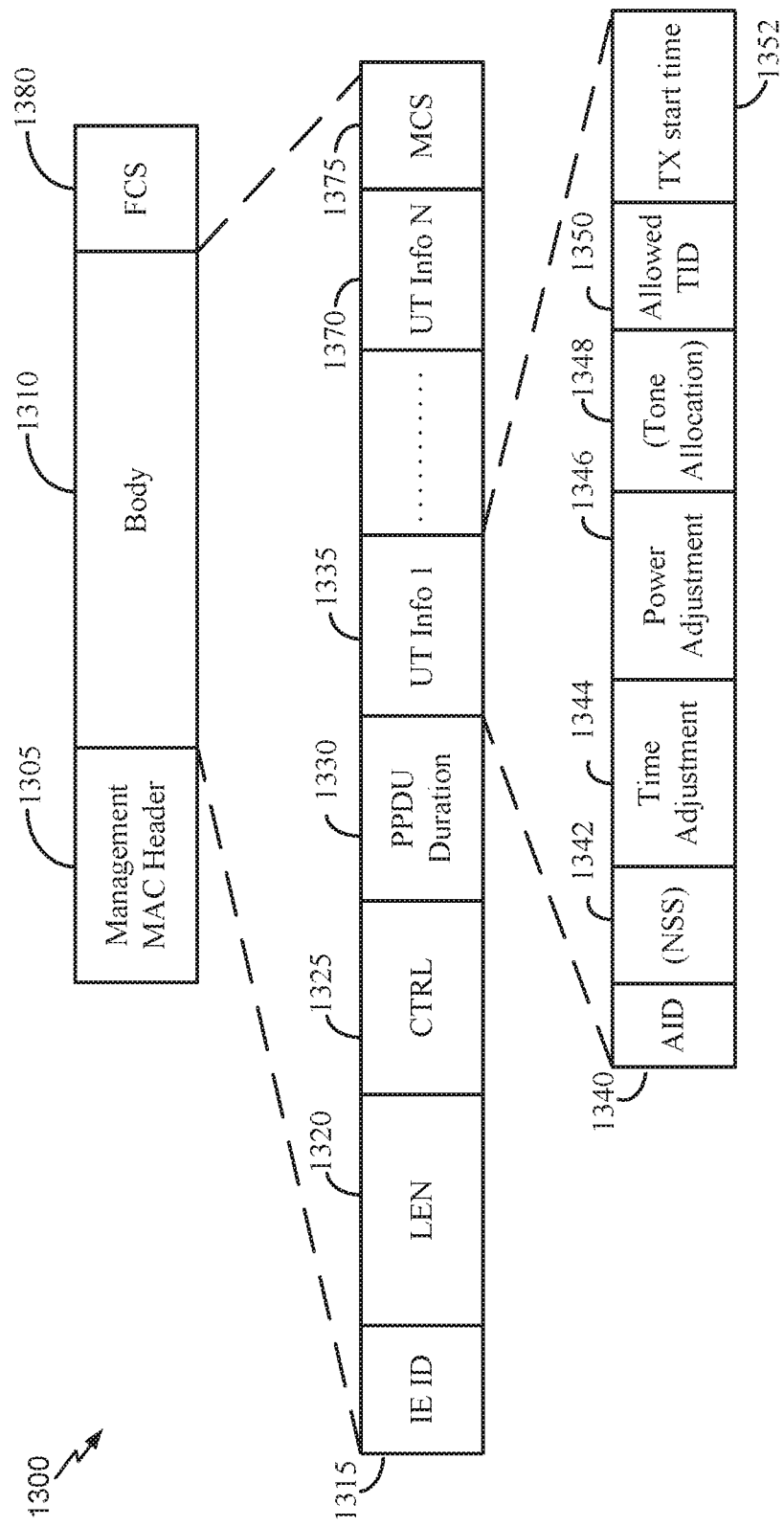
FIG. 13 shows a diagram of another embodiment of a clear to transmit frame.

FIG. 13 is a diagram of an example of a CTX frame 1300 structure. In this embodiment, the CTX frame 1300 is a management frame that includes a Management MAC Header 1305 field, a Body 1310 field, and a FCS 1380 field. The Body 1310 field includes an IE ID 1315 field which identifies an information element (IE), a LEN 1320 field which indicates the length of the CTX frame 1300, a CTRL 1325 field which includes the same information as the CTRL 1020 field, a PPDU Duration 1330 field which indicates the duration of the following UL-MU-MIMO PPDU that the user terminals 120 are allowed to send, a UT Info 1 1335 field and a MCS 1375 field which can indicate the MCS for all the UTs to use in the following UL-MU-MIMO transmission, or an MCS backoff for all the UTs to use in the following UL-MU-MIMO transmission. The UT Info 1 1335 (along with UT Info N 1370) field represent a per UT field that includes AID 1340 field which identifies a UT, a number of spatial streams field (Nss) 1342 field which indicates the number of spatial streams a UT may use (in an UL-MU-MIMO system), a Time Adjustment 1344 field which indicates a time that a UT should adjust its transmission compared to the reception of a trigger frame (the CTX in this case), a Power Adjustment 1346 field which indicates a power backoff a UT should take from a declared transmit power, a Tone Allocation 1348 field which indicates the tones or frequencies a UT may use (in a UL-OFDMA system), an Allowed TID 1350 field which indicates the allowable TID, and a TX start time field 1352 which indicates a start time for the UT to transmit uplink data.

In one embodiment, the CTX frame 1000 or the CTX frame 1300 may be aggregated in an A-MPDU to provide time to a user terminal 120 for processing before transmitting the UL signals. In this embodiment, padding, padding or data may be added after the CTX to allow a user terminal 120 additional time to process the forthcoming packet. One benefit to padding a CTX frame may be to avoid possible contention issues for the UL signals from other user terminals 120, as compared to increasing the interframe space (IFS) as described above. In one aspect, if the CTX is a management frame, additional padding information elements (IEs) may be sent. In one aspect, if the CTX is aggregated in an A-MPDU, additional A-MPDU padding delimiters may be included. Padding delimiters may be end-of-frame (EOF) delimiters (e.g., 4 bytes) or other padding delimiters. In another aspect, the padding may be achieved by adding data, control or Management MPDPUs, as long as they do not require to be processed within the IFS response time. The MPDUs may include an indication indicating to the receiver that no immediate response is required and will not be required by any of the following MPDUs. In another aspect, the user terminals 120 may request to an AP 110 a minimum duration or padding for the CTX frame. In another embodiment, the padding may be achieved by adding PHY OFDMA symbols, which may include undefined bits not carrying information, or may include bit sequences that carry information, as long as they do not need to be processed within the IFS time.

In some embodiments, an AP 110 may initiate a CTX transmission. In one embodiment, an AP 110 may send a CTX message 402 in accordance with regular enhanced distribution channel access (EDCA) contention protocol. In another embodiment, an AP 110 may send a CTX message 402 at scheduled times. In this embodiment, the scheduled times may be indicated by the AP 110 to the user terminals 120 by using a restricted access window (RAW) indication in a beacon which indicates a time reserved for a group of user terminals 120 to access the medium, a target wake time (TWT) agreement with each user terminal 120 which indicates to multiple user terminals 120 to be awake at the same time to take part in a UL-MU-MIMO transmission, or information in other fields. Outside the RAW and TWT a user terminal 102 may be allowed to transmit any frame, or only a subset of frames (e.g., non-data frames). It may also be forbidden to transmit certain frames (e.g., it may be forbidden to transmit data frames). The user terminal 120 may also indicate that it is in sleep state. One advantage to scheduling a CTX is that multiple user terminals 120 may be indicated the same TWT or the same RAW time and may receive a transmission from an AP 110.

Referring to FIGS. 4-6, in conjunction with FIG. 1, the UL-MU-MIMO transmissions 410A and 410B may have the same duration. The user terminals 120 may plan to transmit data and may send a message (e.g., an RTX) to the AP 110 requesting to transmit their data. A message (e.g., CTX message 402) from the AP 110 may indicate a target transmission duration for the UL-MU-MIMO transmissions 410 from user terminals 120 utilizing the UL-MU-MIMO feature. The target transmission duration may also be determined by the AP 110 and the user terminals 120 in the setup phase. The user terminal 120 may determine a planned transmission duration of the planned data for transmission that it has for transmission based on a number of bits in the planned data and the operating and transmission parameters of the user terminal 120 (e.g., level of aggregation and MCS). The user terminal 120 may determine whether the planned transmission duration of the data for transmission fits, exceeds, or falls shown of the target transmission duration. In some circumstances, the user terminal 120 may have planned data for transmission that, when transmitted, will have a planned transmission duration that fits (e.g., is equal to) the target transmission duration such that the user terminal 120 may transmit its data without modification. In other circumstances, the user terminal 120 may have planned data for transmission that, when transmitted, would have a planned transmission duration that exceeds the target transmission duration. In such circumstances the user terminal 120 may change the planned data or its operating and transmission parameters such that the planned transmission duration of the data is decreased to fit the target transmission duration. In other circumstances, the user terminal 120 may have planned data for transmission that, when transmitted, would have a planned transmission duration that falls short of the target transmission duration. In such circumstances the user terminal 120 may change the planned data or its operating or transmission parameters such that the planned transmission duration of the data is increased to fit the target transmission duration.

In some aspects, the AP 110 may restrict the parameters that the user terminals 120 may change. The AP 110 may indicate such restrictions in a trigger frame. In one aspect, the AP 110 may specify a target transmission duration for the user terminals 120 and the user terminals 120 may each determine their UL PPDU duration, data payload size, MCS, and amount of fill data. In another aspect the AP 110 may specify a target transmission duration and a UL PPDU duration for the user terminals 120 and the user terminals 120 may each determine their data payload size, MCS, and amount of fill data. In another aspect, the AP 110 may specify a target transmission duration, UL PPDU duration, and MCS for the user terminals 120 and the user terminals 120 may each adjust their data payload size and amount of fill data.

In some aspects, the user terminals 120 may send information to the AP 110 indicating their data payload size. In one such aspect, the AP 110 may determine an amount of fill data for each user terminal 120 based on the data payload sizes of the user terminals 120 and the AP 110 may indicate an amount of fill data to use, a target transmission duration, a UL PPDU duration, and an MCS for each of the user terminals 120 in the trigger frame. In this aspect, each of the user terminals 120 may determine their data payload size. In another such aspect, the AP 110 may indicate a target transmission duration, a UL PPDU duration, data payload size, MCS, and an amount of fill data for each of the user terminals 120. In another aspect, the AP 110 may indicate a level of data aggregation for each user terminal 120 to use as discussed further discussed below. Accordingly, the user terminals 120 may determine operating and transmission parameter adjustments which are not specified by the AP 110 in the trigger frame. FIGS. 14-22 show examples of changes that user terminals 120 may make to their data for transmission or their operating and transmission parameters in order to fit the target transmission duration.

Figure 14:
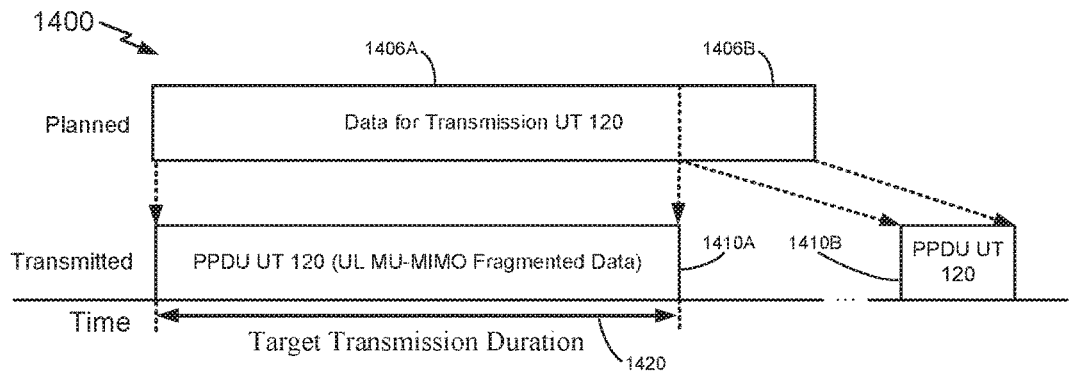
FIG. 14 is a time sequence diagram that shows a user terminal fragmenting its data for transmission to fit a target transmission duration for an uplink multi-user multiple-input multiple-output transmission during a transmission opportunity.

FIG. 14 is a time sequence diagram 1400 that shows a user terminal 120 fragmenting its planned data for transmission to fit a target transmission duration 1420 for a UL-MU-MIMO transmission during a transmission opportunity. The dashed arrows in FIG. 14 indicate that a duration of a first PPDU 1410A as transmitted by the user terminal 120 remains the same as a planned transmission duration of a first portion of the data for transmission 1406A. As described above, an AP 110 may indicate the target transmission duration 1420 in a message granting a transmission opportunity (e.g., a CTX message) to the user terminal 120. As shown in FIG. 14, the user terminal 120 may have planned data for transmission 1406 that, when transmitted, has a planned transmission duration that exceeds the target transmission duration 1420. The user terminal 120 may change the planned data 1406 to fit the target transmission duration 1420 by fragmenting the planned data 1406 into a first portion of data 1406A and a second portion of data 1406B. The first PPDU 1410A including the first portion data 1406A may, when transmitted by the user terminal 120 according to a UL-MU-MIMO operating mode, have a transmission duration that fits the target transmission duration 1420. The second portion of the data 1406B may be transmitted by the user terminal 120 in a second PPDU 1410B at a later time (e.g., during a subsequent transmission opportunity). As such, the user terminal 120 may build the first PPDU 1410A such that the length of the PPDU matches the target transmission duration indicated by the AP 110.

Figure 15:
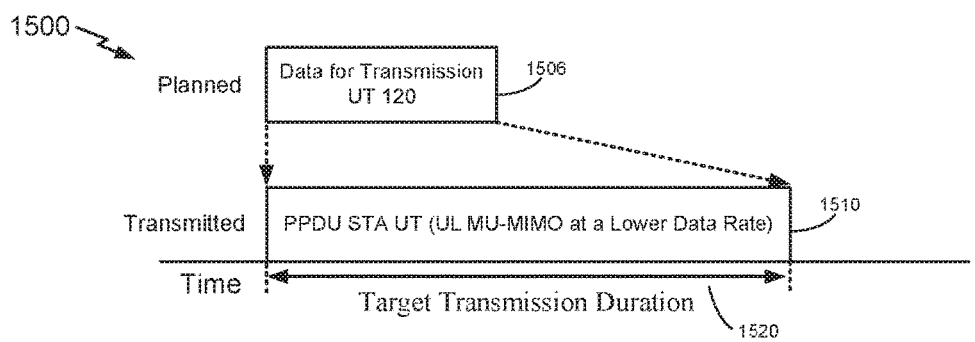
FIG. 15 is a time sequence diagram that shows a user terminal decreasing its transmission data rate to fit a target transmission duration for an uplink multi-user multiple-input multiple-output transmission during a transmission opportunity.

FIG. 15 is a time sequence diagram 1500 that shows a user terminal 120 decreasing its transmission data rate to fit a target transmission duration 1520 for a UL-MU-MIMO transmission during a transmission opportunity. The dashed arrows in FIG. 15 indicate an increase in transmission duration resulting from the user terminal 120 decreasing its planned transmission data rate. As described above, an AP 110 may indicate the target transmission duration 1520 in a message granting a transmission opportunity (e.g., trigger frame or CTX message) to the user terminal 120. As shown in FIG. 15, the user terminal 120 may have planned data for transmission 1506 that, when transmitted according to planned operating and transmission parameters, has a planned transmission duration that falls short of the target transmission duration 1520. Accordingly, the user terminal 120 may change its operating and transmission parameters to fit the target transmission duration 1520. For example, the user terminal 120 may transmit the data 1506 at a lower data rate (e.g., slower MCS) to fit the target transmission duration 1520. The user terminal 120 may also adjust a coding scheme and a guard interval for the transmission of uplink data. As described above, the AP 110 may determine and indicate the MCS adjustment for each the user terminal 120 in the trigger frame or each user terminal 120 may determine its MCS adjustment itself. A PPDU 1510 including the data 1506 may, when transmitted by the user terminal 120 at the lower data rate according to a UL-MU-MIMO operating mode, have a transmission duration that fits the target transmission duration 1520.

Figure 16:
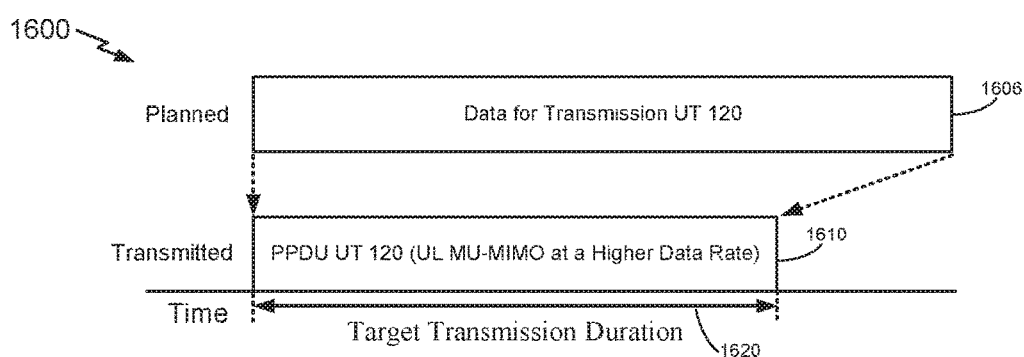
FIG. 16 is a time sequence diagram that shows a user terminal increasing its transmission data rate to fit a target transmission duration for an uplink multi-user multiple-input multiple-output transmission during a transmission opportunity.

FIG. 16 is a time sequence diagram 1600 that shows a user terminal 120 increasing its transmission data rate to fit a target transmission duration 1620 for a UL-MU-MIMO transmission during a transmission opportunity. The dashed arrows in FIG. 16 indicate a decrease in transmission duration resulting from the user terminal 120 increasing the transmission data rate of the data for transmission 1606 to produce the PPDU 1610 as transmitted by the user terminal 120. As described above, an AP 110 may indicate the target transmission duration 1620 in a message granting a transmission opportunity (e.g., a CTX message) to the user terminal 120. As shown in FIG. 16, the user terminal 120 may have planned data for transmission 1606 that, when transmitted, would have a planned transmission duration that exceeds the target transmission duration 1620. The user terminal 120 may transmit the data 1606 at a higher data rate (e.g., faster MCS) to fit the target transmission duration 1620. The user terminal 120 may also adjust a coding scheme and a guard interval for the transmission of uplink data. As described above, the AP 110 may determine and indicate the MCS adjustment for each the user terminal 120 in the trigger frame or each user terminal 120 may determine its MCS adjustment itself. A PPDU 1610 including the data 1606 may, when transmitted by the user terminal 120 at the higher data rate according to a UL-MU-MIMO operating mode, have a transmission duration that fits the target transmission duration 1620.

Figure 17:
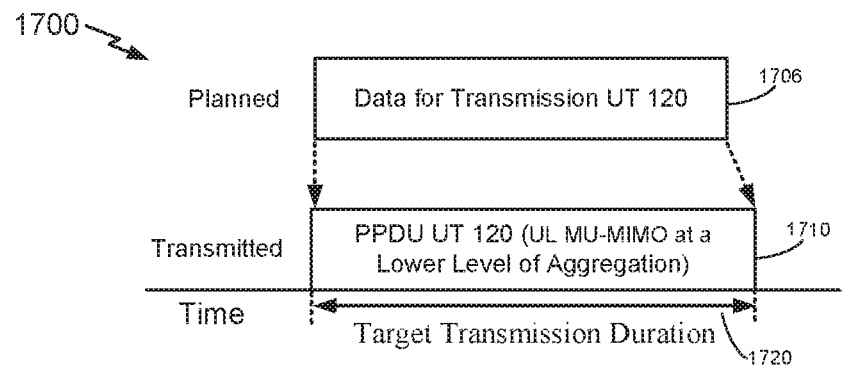
FIG. 17 is a time sequence diagram that shows a user terminal decreasing its level of aggregation to fit a target transmission duration for an uplink multi-user multiple-input multiple-output transmission during a transmission opportunity.

FIG. 17 is a time sequence diagram 1700 that shows a user terminal 120 decreasing its level of aggregation to fit a target transmission duration 1720 for a UL-MU-MIMO transmission during a transmission opportunity. The dashed arrows in FIG. 17 indicate an increase in transmission duration resulting from the user terminal 120 decreasing the level of aggregation for the data for transmission 1706 to produce the PPDU 1710 as transmitted by the user terminal 120. As described above, an AP 110 may indicate the target transmission duration 1720 in a message granting a transmission opportunity (e.g., a CTX message) to the user terminal 120. As shown in FIG. 17, the user terminal 120 may have planned data for transmission 1706 that, when transmitted, would have a planned transmission duration that falls short of the target transmission duration 1720. The user terminal 120 may decrease a level of data aggregation in a medium access control (MAC) protocol data unit (A-MPDU) or a level of data aggregation in a MAC service data unit (A-MSDU) to fit the target transmission duration 1720. The AP 110 may determine and indicate the level of aggregation for each the user terminal 120 in the trigger frame or each user terminal 120 may determine its level of aggregation itself. A PPDU 1710 including the data 1706 may, when transmitted by the user terminal 120 at the lower level of data aggregation according to a UL-MU-MIMO operating mode, have a transmission duration that fits the target transmission duration 1720.

Figure 18:
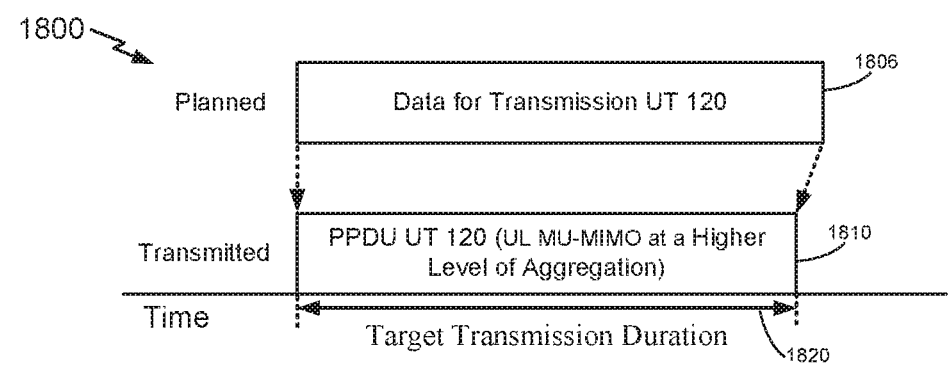
FIG. 18 is a time sequence diagram that shows a user terminal increasing its level of aggregation to fit a target transmission duration for an uplink multi-user multiple-input multiple-output transmission during a transmission opportunity.

FIG. 18 is a time sequence diagram 1800 that shows a user terminal 120 increasing its level of aggregation to fit a target transmission duration 1820 for a UL-MU-MIMO transmission during a transmission opportunity. The dashed arrows in FIG. 18 indicate a decrease in transmission duration resulting from the user terminal 120 increasing the level of aggregation for the planned data for transmission 1806 to produce the PPDU 1810 as transmitted by the user terminal 120. As described above, an AP 110 may indicate the target transmission duration 1820 in a message granting a transmission opportunity (e.g., a CTX message) to the user terminal 120. As shown in FIG. 18, the user terminal 120 may have data for transmission 1806 that, when transmitted, would have a planned transmission duration that exceeds the target transmission duration 1820. The user terminal 120 may increase a level of data aggregation in an A-MPDU or a level of data aggregation in an A-MSDU to fit the target transmission duration 1820. The AP 110 may determine and indicate the level of aggregation for each the user terminal 120 in the trigger frame or each user terminal 120 may determine its level of aggregation itself. A PPDU 1810 including the data 1806 may, when transmitted by the user terminal 120 at the higher level of data aggregation according to a UL-MU-MIMO operating mode, have a transmission duration that fits the target transmission duration 1820.

Figure 19:
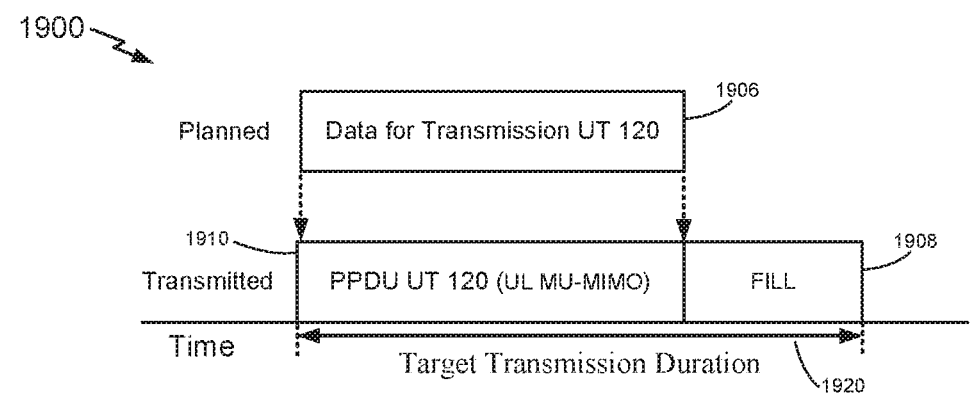
FIG. 19 is a time sequence diagram that shows a user terminal adding fill data 1908 to fit a target transmission duration for an uplink multi-user multiple-input multiple-output transmission during a transmission opportunity.

FIG. 19 is a time sequence diagram 1900 that shows a user terminal 120 adding fill data 1908 to fit a target transmission duration 1920 for a UL-MU-MIMO transmission during a transmission opportunity. The dashed arrows in FIG. 19 indicate that the transmission duration of a PPDU 1910 as transmitted by the user terminal 120 remains the same as the data for transmission 1906, except for the fill data 1908. As described above, an AP 110 may indicate the target transmission duration 1920 in a message granting a transmission opportunity (e.g., a CTX message) to the user terminal 120. As shown in FIG. 19, the user terminal 120 may have planned data for transmission 1906 that, when transmitted, would have a planned transmission duration that falls short of the target transmission duration 1920. The user terminal 120 may transmit a PPDU 1910 including base data (e.g., the data for transmission 1906) and may also transmit fill data 1908 according to a UL-MU-MIMO operating mode during the transmission opportunity to fit the target transmission duration 1920. The AP 110 may determine and indicate the amount of fill data for each the user terminal 120 in the trigger frame or each user terminal 120 may determine the amount of fill data itself. In other embodiments the fill data 1908 may be transmitted before the PPDU 1910. The fill data 1908 may include, for example, end-of-frame (EOF) padding delimiters, subframe pad octets, or A-MPDU EOF subframes. The fill data 1908 may also be transmitted before the PPDU 1910. In another embodiment, the fill data 1908 may be added to the beginning of an A-MPDU. A combined transmission duration of the PPDU 1910 including the base data and the fill data 1908 may fit the target transmission duration 1920.

Figure 20:
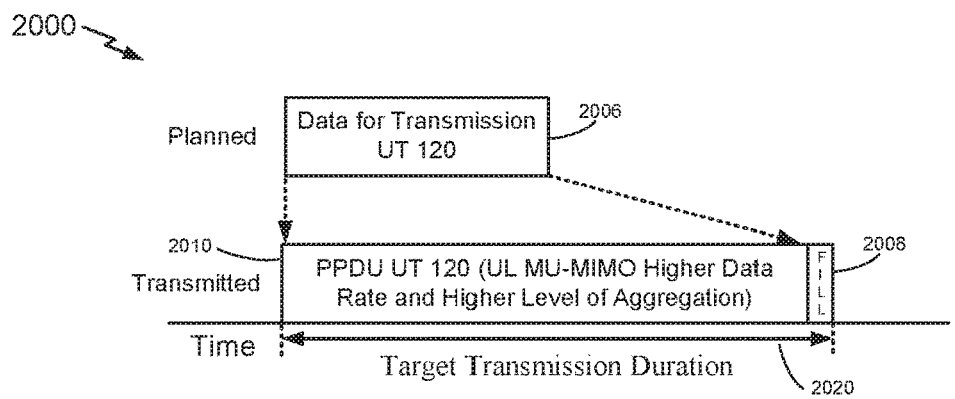
FIG. 20 is a time sequence diagram that shows a user terminal decreasing its transmission data rate, decreasing its level of aggregation, and adding fill data to fit a target transmission duration for an uplink multi-user multiple-input multiple-output transmission during a transmission opportunity.

FIG. 20 is a time sequence diagram 2000 that shows a user terminal 120 decreasing its transmission data rate, decreasing its level of aggregation, and adding fill data 2008 to fit a target transmission duration 2020 for a UL-MU-MIMO transmission during a transmission opportunity. The dashed arrows in FIG. 20 indicate the change in transmission duration resulting from the user terminal 120 increasing the level of aggregation and increasing the data rate for the data for transmission 2006 to produce the PPDU 2010 as transmitted by the user terminal 120. As described above, an AP 110 may indicate the target transmission duration 2020 in a message granting a transmission opportunity (e.g., a CTX message) to the user terminal 120. As shown in FIG. 20, the user terminal 120 may have planned data for transmission 2006 that, when transmitted, would have a planned transmission duration that falls short of the target transmission duration 2020. The user terminal 120 may decrease a level of data aggregation in an A-MPDU or an A-MSDU and may transmit the data 2006 and fill data 2008 at a lower data rate (e.g., by adjusting its MCS) to fit the target transmission duration 2020. As discussed above, the AP 110 may determine and indicate the level of data aggregation and the MCS for each the user terminal 120 in the trigger frame or each user terminal 120 may determine the level of data aggregation and the MCS itself. A combined transmission duration of the PPDU 2010 and the fill data 2008 may fit the target transmission duration 2020.

Figure 21:
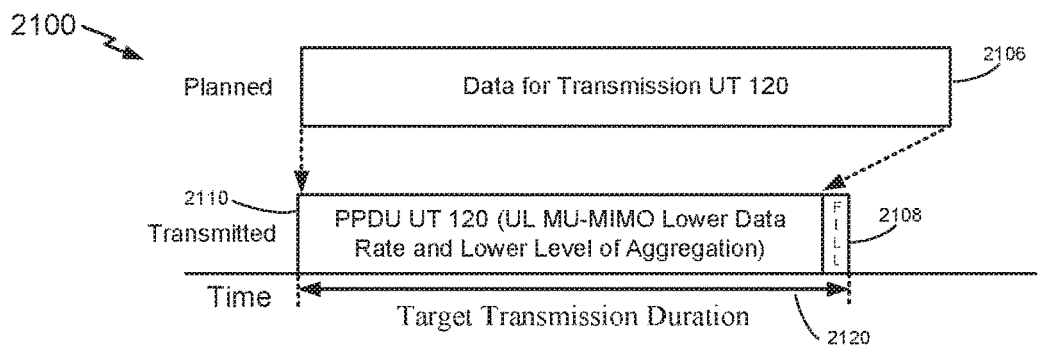
FIG. 21 is a time sequence diagram that shows a user terminal increasing its transmission data rate, increasing its level of aggregation, and adding fill data to fit a target transmission duration for an uplink multi-user multiple-input multiple-output transmission during a transmission opportunity.

FIG. 21 is a time sequence diagram 2100 that shows a user terminal 120 increasing its transmission data rate, increasing its level of aggregation, and adding fill data 2108 to fit a target transmission duration 2120 for a UL-MU-MIMO transmission during a transmission opportunity. The dashed arrows in FIG. 21 indicate the change in transmission duration resulting from the user terminal 120 decreasing the level of aggregation and decreasing the data rate for the data for transmission 2106 to produce the PPDU 2110 as transmitted by the user terminal 120. As described above, an AP 110 may indicate the target transmission duration 2120 in a message granting a transmission opportunity (e.g., a CTX message) to the user terminal 120. As shown in FIG. 21, the user terminal 120 may have planned data for transmission 2106 that, when transmitted, would have a planned transmission duration that exceeds the target transmission duration 2120. The user terminal 120 may increase a level of data aggregation in an A-MPDU or an A-MSDU and may transmit the data 2006 and fill data 2008 at a higher data rate (e.g., by adjusting its MCS) to fit the target transmission duration 2120. As discussed above, the AP 110 may determine and indicate the level of data aggregation and the MCS for each the user terminal 120 in the trigger frame or each user terminal 120 may determine the level of data aggregation and the MCS itself. A combined transmission duration of a PPDU 2110, including the data 2106, and the fill data 2008 may fit the target transmission duration 2120.

Figure 22:
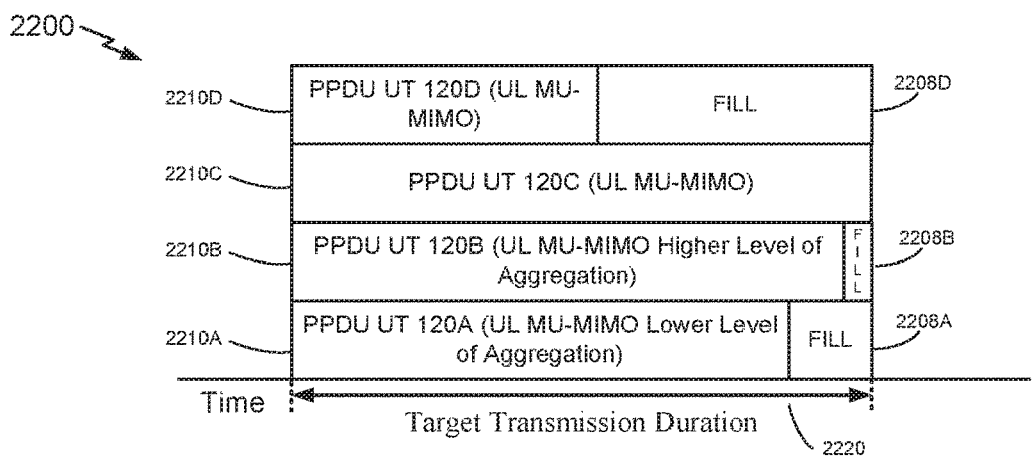
FIG. 22 is a time sequence diagram that shows user terminals concurrently transmitting data during a transmission opportunity for a duration that fits a target transmission duration.

FIG. 22 is a time sequence diagram 2200 that shows user terminals 120A-D concurrently transmitting data during a transmission opportunity for a duration that fits a target transmission duration 2220. As described above, an AP 110 may indicate the target transmission duration 2220 in a message granting a transmission opportunity (e.g., a CTX message) to the user terminals 120A-D. As shown in FIG. 22, the user terminals 120A-D may transmit data (e.g., a PPDU or fill data) to fit the target transmission duration 2220. The user terminal 120A may decrease a level of data aggregation in an A-MPDU or an A-MSDU as described above and may transmit fill data 2208A and a PPDU 2210A to fit the target transmission duration 2220. The user terminal 120B may increase a level of data aggregation in an A-MPDU or an A-MSDU as described above and may transmit fill data 2208B and a PPDU 2210B to fit the target transmission duration 2220. The user terminal 120C may have data for transmission that when transmitted in a PPDU 2210C, fits the target transmission duration 2220 without modifying a level of data aggregation or adding fill data. The user terminal 120D may transmit a PPDU 2210D and fill data 2208D to fit the target transmission duration 2220. In other embodiments, the user terminals 120 may use any combination of the changes in data or operating and transmission parameters shown in FIGS. 14-21 in order to fit the target transmission duration. One of the benefits of having all of the UL-MU-MIMO transmissions from user terminals 120A-D be the same length is that the power level of the transmissions will remain constant, thereby reducing the negative effects of power fluctuations on the receivers.

Figure 23:
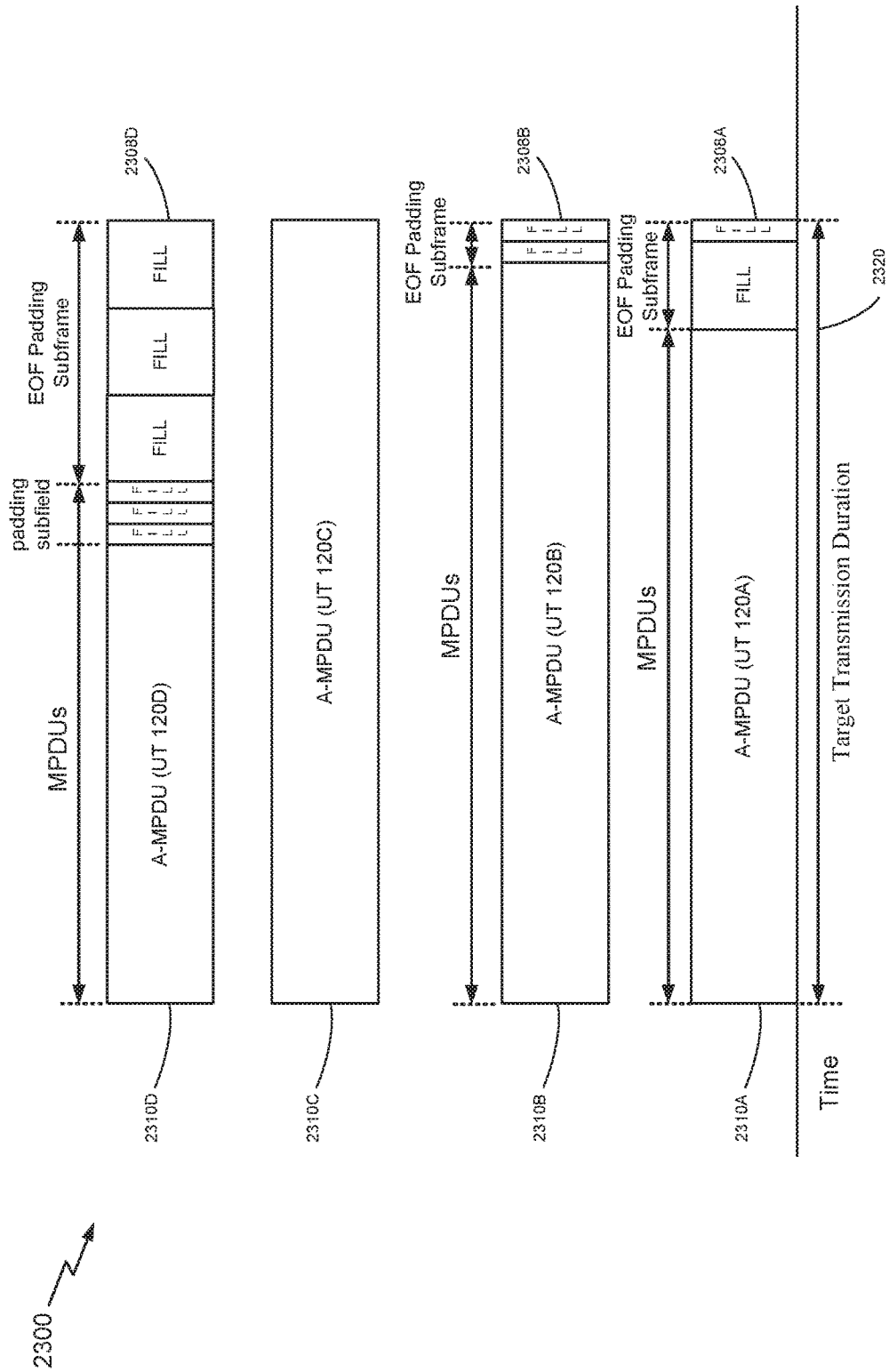
FIG. 23 is another time sequence diagram that shows user terminals utilizing fill subframes to fill a target transmission duration.

FIG. 23 is another time sequence diagram 2300 that shows user terminals utilizing fill subframes to fill a target transmission duration. As illustrated, user terminals 120A-D may each transmit a PSDU that is of a target transmission duration 2320. Each PSDU may comprise an A-MPDU frame 2310A-D, and one or more of the A-MPDU frames 2310A-D may include padding (illustrated as "fill" 2308A, 2308B, and 2308D). In some aspects, the PSDU may be included in a high-efficiency (HE) trigger based (TB) PPDU. In some aspects, prior to the transmission of the MPDU frames, one or more transmission parameters may be transmitted by an AP 110 to each of the user terminals 120A-D. For example, MCS, duration, transmission power, or other PHY parameters may be communicated by the AP 110. In an embodiment, these parameters can be included in a trigger frame, which can be similar to the CTX 402. In an aspect, the AP 110 may transmit the target transmission duration 2320 itself. In another aspect, the UTs 120A-D may determine the target transmission duration 2320 based on one or more of the transmission parameters communicated by the AP 110. Once the UTs 120 know the value of the target transmission duration 2320, they may utilize the value to generate their respective A-MPDU frames 2310A-D.

Various methods may be utilized for generating the MPDU frames 2310A-D. For example, a UT 120 may start by creating an A-MPDU frame that contains one A-MPDU data "subframe." Thereafter, the UT 120 may determine whether additional A-MPDU data subframes or A-MPDU delimiter subframes may be added to the A-MPDU frame based at least upon the value of the target transmission duration 2320. In an aspect, a UT 120 may only add an A-MPDU data subframe to the A-MPDU frame if the length of the A-MPDU data subframe is greater than zero and if adding the A-MPDU data subframe to the A-MPDU frame will not cause a length of the A-MPDU frame to exceed the target transmission duration 2320. In another aspect, a UT 120 may only add an A-MPDU delimiter subframe to the A-MPDU frame if the length of the A-MPDU delimiter subframe is equal to zero and if an EOF field of the A-MPDU delimiter subframe is set to zero. The length of an A-MPDU subframe may be indicated in a length field of each MPDU (e.g., an A-MPDU data subframe or an A-MPDU delimiter subframe).

In some aspects, a UT 120 may be restricted on the contents, the length, or the start spacing of MPDUs contained in the A-MPDU frame or the A-MPDU frame itself. In some aspects, one or more of these restrictions may be determined during association between a UT 120 and an AP 110. In various aspects, one or more of these restrictions may be communicated to the UTs 120 through the use of trigger frames or other messages. Restricting the contents, length, or start spacing may insure that a receiving device is able to properly receive and interpret each MPDU in the A-MPDU frame. In some aspects, a UT 120 may not add an A-MPDU subframe with an EOF field equal to '0' after any A-MPDU subframe with the EOF field set to '1'. In some aspects, a UT 120 may not add an A-MPDU subframe with the EOF field set to '1' and an MPDU length field set to '0' before an A-MPDU subframe that contains a very high throughput (VHT) single MPDU.

Once a UT 120 has added as many MPDUs to the A-MPDU frame as desired, a UT 120 may need to add padding information to the A-MPDU frame so that the length of the A-MPDU frame is equal to the target transmission duration 2320. For example, as illustrated, the length of the A-MPDU frames 2310A, 2310B, and 2310D may be short of the target transmission duration 2320. Padding information may comprise a sequence of bits set to '1' or '0', one or more A-MPDU padding subframes, and/or some other information which an AP 110 may understand as padding. In order to add padding to an A-MPDU frame, a UT 120 may determine whether the current length of the A-MPDU frame is divisible by four (e.g., whether current length mod 4 !=0). In some aspects, the length of the A-MPDU frame may be expressed in terms of a number of octets. If the current length is not divisible by four, and the current length is less than the target transmission duration 2320, the UT 120 may add an octet of padding to the final A-MPDU subframe's padding subfield. In certain implementations, the UT 120 increments the current value of the A-MPDU frame length by one. The UT 120 may repeat this process until the current length is divisible by four. For example, as illustrated, the length of A-MPDU frame 2310D mod 4=1. Therefore, three octets of padding may be added to the A-MPDU frame 2310D.

Additionally or alternatively, in order to add padding to an A-MPDU frame, a UT 120 may determine whether the sum of the current length of the A-MPDU frame plus four is less than the target transmission duration 2320. If the value of the current length is at least four less than the target transmission duration 2320, the UT 120 may add an EOF padding subframe to an EOF padding subframe field in the A-MPDU frame. In certain implementations, the UT increments the current value of the A-MPDU frame length by four. In an aspect, the length of an EOF padding subframe may be four octets. The UT 120 may repeat this process until the current length is less than four (octets) smaller than the target transmission duration 2320. For example, as illustrated, the length of A-MPDU frame 2310A+4 is less than the target transmission duration 2320. Therefore, an EOF padding subframe may be added to an EOF padding subframe field of the A-MPDU frame 2310A. In some aspects, a UT 120 may determine the last subframe in an A-MPDU frame 2310 which has a delimiter with a length greater than zero, and may set an EOF bit of the identified delimiter to be equal to '1'. In accordance with these aspects, the following subframes, if any, can be delimiter subframes, each with a length equal to zero and an EOF bit equal to '1'.

Additionally or alternatively, in order to add padding to an A-MPDU frame, a UT 120 may determine whether the current length of the A-MPDU frame is less than the target transmission duration 2320. If the value of the current length is less than the target transmission duration 2320, the UT 120 may add an octet of padding to an EOF padding octets subfield in the A-MPDU frame, and increment the current value of the A-MPDU frame length by one. The UT 120 may repeat this process until the current length equal to the target transmission duration 2320. For example, as illustrated, the length of A-MPDU frame 2310B is less than the target transmission duration 2320. Therefore, an octet of padding may be added to an EOF padding octets subfield of the A-MPDU frame 2310B.

Figure 24:
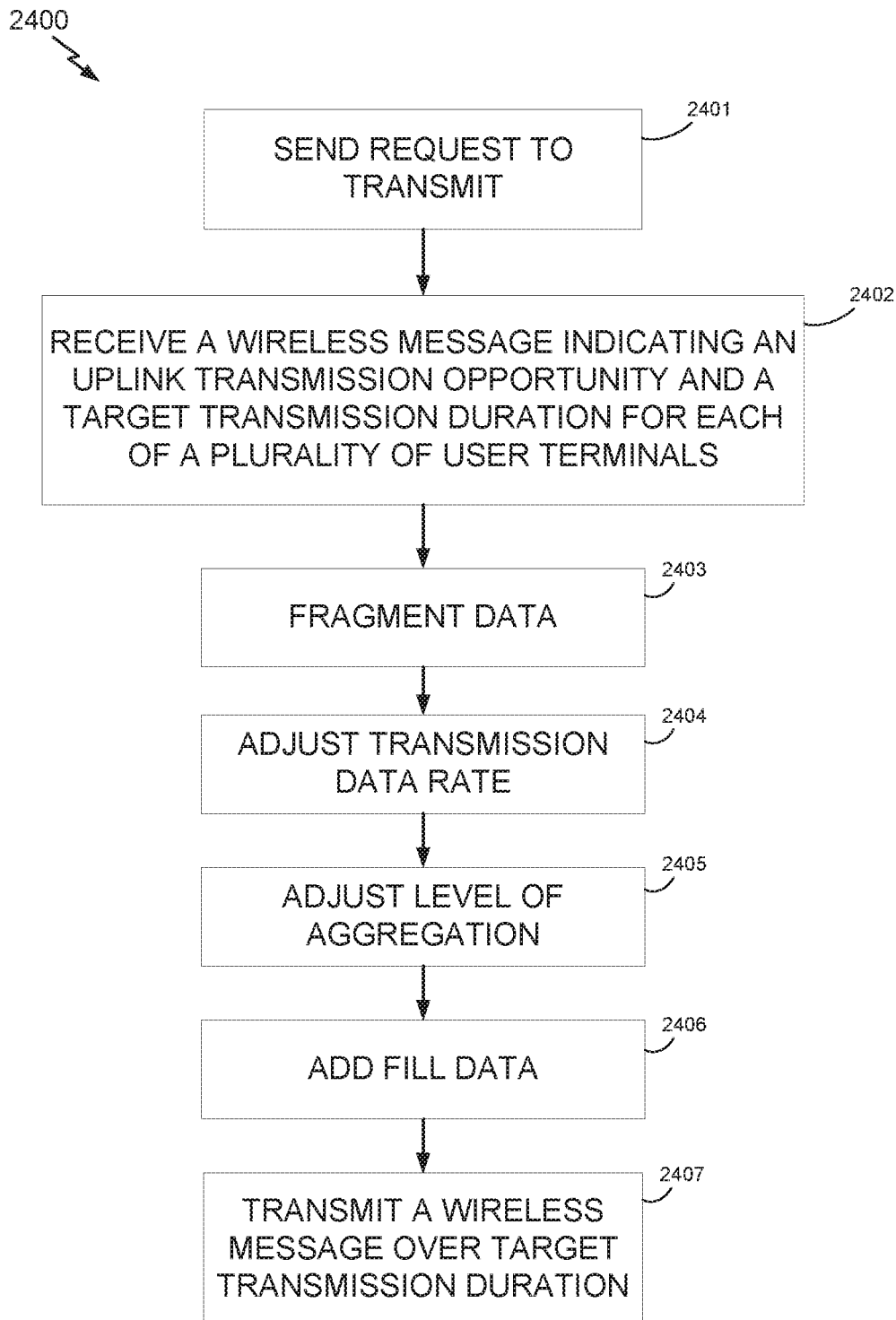
FIG. 24 is a flow chart of a method for selecting data for transmission or operating parameters such that a duration of an uplink multi-user multiple-input multiple-output transmission fills a target transmission duration.

FIG. 24 is a flow chart of a method 2400 for changing data for transmission or operating parameters such that a duration of an UL-MU-MIMO transmission fits a target transmission duration. At block 2401, a user terminal 120 may send a request to transmit (e.g., an RTX) to an AP 110 as described herein. At block 2402, the user terminal 120 may receive a wireless message from the AP 110 (e.g., a CTX) indicating an uplink transmission opportunity and a target transmission duration for each of a plurality of user terminals 120 as described herein.

At block 2403, the user terminal 120 may fragment the data for transmission as described herein. At block 2404, the user terminal 120 may adjust its transmission data rate to fit the target transmission duration as described herein. At block 2405, the user terminal 120 may adjust a level of data aggregation to fit the target transmission duration as described herein. At block 2406, the user terminal 120 may add fill data to fit the target transmission duration as described herein. Each of the steps at blocks 2403, 2404, 2405, and 2406 are optional and the user terminal 120 may perform any combination of these steps to fit the target transmission duration as described herein. At block 2407, the user terminal 120 may transmit a message over the target transmission duration.

Figure 25:
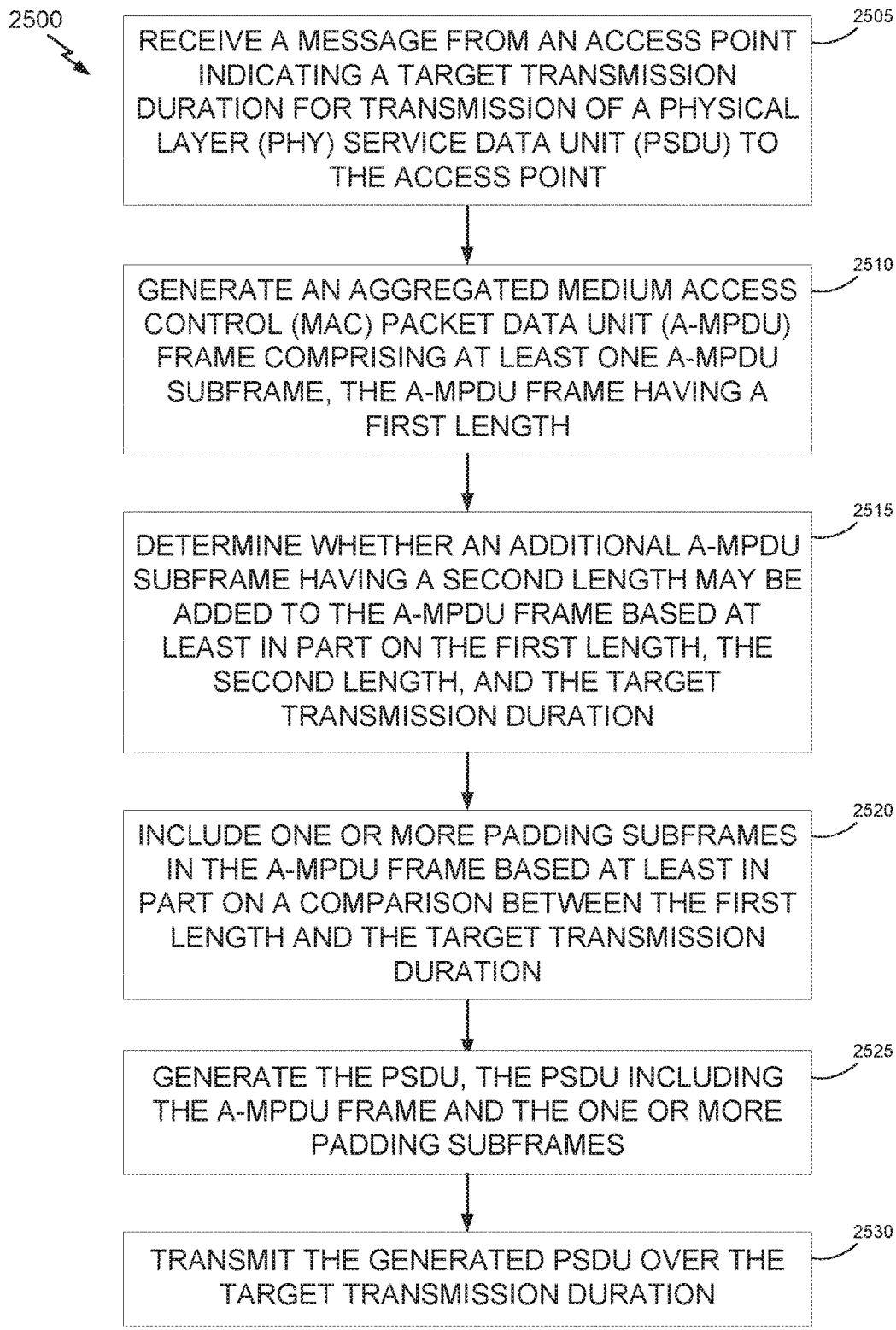
FIG. 25 is a flowchart illustrating a method for wireless communication involving the generation of an A-MPDU for transmission.

FIG. 25 is a flowchart illustrating a method 2500 for wireless communication involving the generation of an A-MPDU for transmission. In an aspect, method 2500 may be implemented by a UT 120. At block 2505, the UT 120, for example, receives a message from an AP 110 indicating a target transmission duration for transmission of a physical layer (PHY) service data unit (PSDU) to the AP 110. In some aspects, the message from the AP 110 further indicates a modulation or coding rate and a transmission power level. At block 2510, the UT 120, for example, generates an aggregated medium access control (MAC) packet data unit (A-MPDU) frame comprising at least one A-MPDU subframe, the A-MPDU frame having a first length. At block 2515, the UT 120, for example, determines whether an additional A-MPDU subframe having a second length may be added to the A-MPDU frame based at least in part on the first length, the second length, and the target transmission duration. For example, if the first length plus the second length is less than the target transmission duration, the UT 120 may add the A-MPDU subframe to the A-MPDU frame. At block 2520, the UT 120, for example, includes one or more padding subframes in the A-MPDU frame based at least in part on a comparison between the first length and the target transmission duration. For example, the UT 120 may add a plurality of bits to the A-MPDU frame sufficient to increase the first length to be equal to the target transmission duration. In some aspects, the plurality of bits can comprise padding within an A-MPDU subframe's padding field, an end-of-frame padding delimiter, a subframe padding octet, and/or an A-MPDU end-of-frame subframe.

Additionally or alternatively, as part of the method 2500, the UT 120, for example, may determine whether a remainder of the first length divided by four is equal to zero. In some implementations, the UT 120 may include an octet of padding in the A-MPDU frame when the first length is less than the target transmission duration and the remainder is not equal to zero. In some implementations, the UT 120 may increment the first length by one for each octet of padding included in the A-MPDU frame. Additionally or alternatively, as part of the method 2500, the UT 120, for example, may determine whether a difference between the target transmission duration and the first length is greater than four. In some implementations, the UT 120 may include an end-of-frame padding subframe in the A-MPDU frame when the difference is greater than four. In some implementations, the UT 120 may increment the first length by four for each end-of-frame padding subframe included in the padding information. Additionally or alternatively, as part of the method 2500, the UT 120, for example, may include a final end-of-frame padding subframe in the A-MPDU frame. In some implementations, the UT 120 may include an octet of padding in the final end-of-frame padding subframe when the first length is less than the target transmission duration. In some implementations, the UT 120 may increment the first length by one for each octet of padding included in the final end-of-frame padding subframe.

At block 2525, the UT 120, for example, generates the PSDU, the PSDU including the A-MPDU frame and the one or more padding subframes. At block 2530, the UT 120, for example, transmits the generated PSDU from over the target transmission duration. In some aspects, the UT 120, for example, can transmit the PSDU concurrently with a plurality of UTs 120 (e.g., UTs 120A-D) over the target transmission duration. In some aspects, a transmission power level of the transmitted PSDU is substantially constant during the target transmission duration. In some aspects, the UT 120, for example, may utilize a transmission data rate, indicated in the message, for transmitting the PSDU. In some aspects, the UT 120, for example, may utilize a level of aggregation, indicated in the message, for transmitting the PSDU. In some aspects, the UT 120, for example, may utilize an uplink transmission opportunity, determined by the user terminal during a setup phase, for transmitting the PSDU. In an embodiment, the PSDU can be transmitted within a PHY convergence protocol data unit (PPDU).

Figure 26:
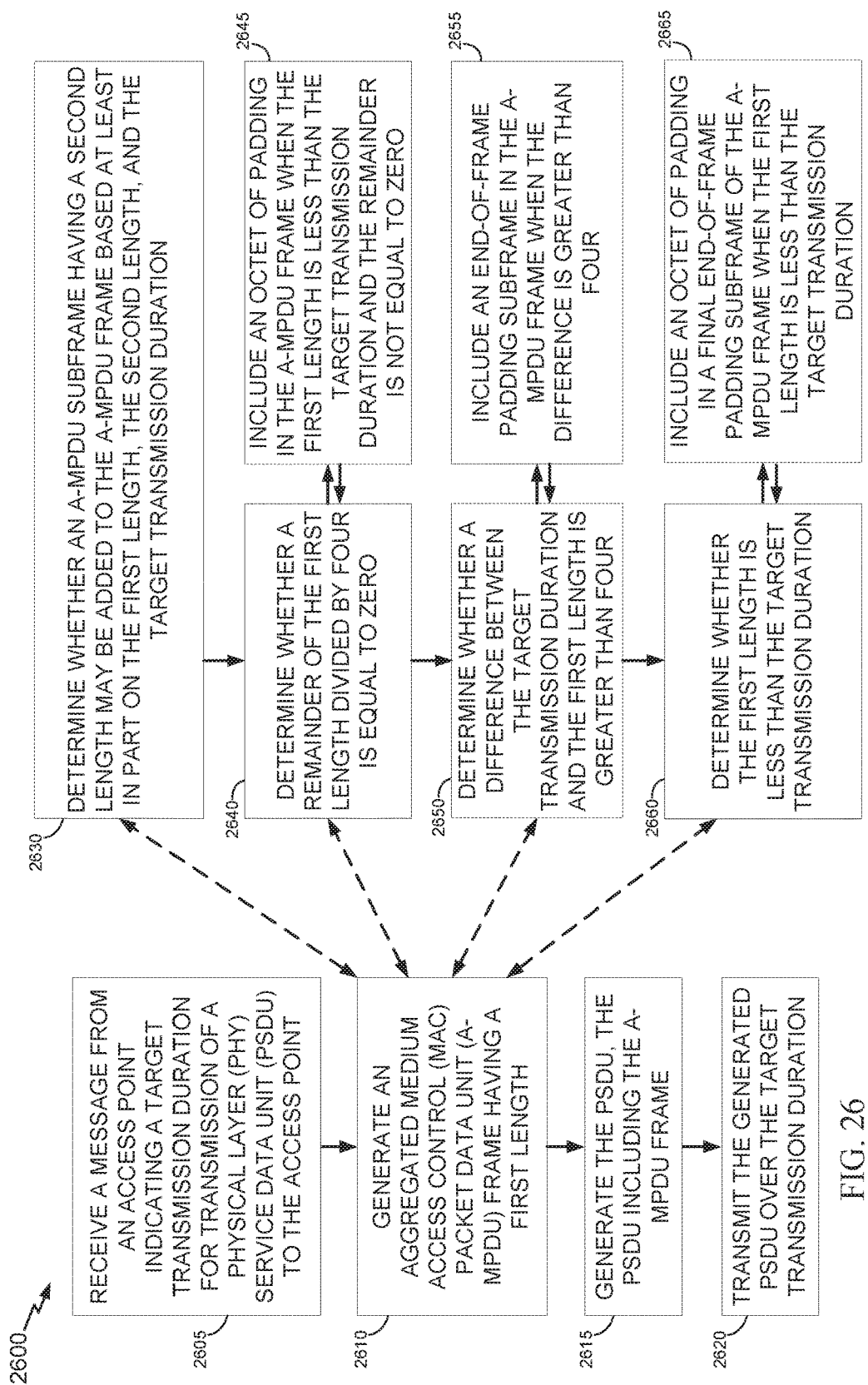
FIG. 26 is another flowchart illustrating a method for wireless communication including multiple alternative embodiments of generating padding.

FIG. 26 is another flowchart illustrating another method 2600 for wireless communication including multiple alternative embodiments of generating padding. In an aspect, method 2600 may be implemented by a UT 120. At block 2605, the UT 120, for example, receives a message from an AP 110 indicating a target transmission duration for transmission of a physical layer (PHY) service data unit (PSDU) to the AP 110. In some aspects, the message from the AP 110 further indicates a modulation or coding rate and a transmission power level. At block 2610, the UT 120, for example, generates an aggregated medium access control (MAC) packet data unit (A-MPDU) frame having a first length. At block 2615, the UT 120, for example, generates the PSDU, the PSDU including the A-MPDU frame. At block 2620, the UT 120, for example, transmits the generated PSDU over the target transmission duration.

As illustrated, after the A-MPDU frame is generated at block 2610, the UT 120, for example, may optionally proceed to one of blocks 2630, 2640, 2650, or 2660. At block 2630, the UT 120, for example, determines whether an A-MPDU subframe having a second length may be added to the A-MPDU frame based at least in part on the first length, the second length, and the target transmission duration. For example, if the first length plus the second length is less than the target transmission duration, the UT 120 may add the A-MPDU subframe to the A-MPDU frame. Additionally or alternatively, the method 2600 may proceed to block 2640 from block 2610 or 2630, where the UT 120, for example, may determine whether a remainder of the first length divided by four is equal to zero. Thereafter, method 2600 may proceed to block 2645, where the UT 120 may include an octet of padding in the A-MPDU frame when the first length is less than the target transmission duration and the remainder is not equal to zero. Optionally, the UT 120 can increment the first length by one for each octet of padding included in the A-MPDU frame. After block 2645, the method 2600 may return to block 2640. Optionally, after block 2640, the method 2600 may return to block 2610.

Additionally or alternatively, after block 2610, 2630, or 2640, the method 2600 may proceed to block 2650 where, the UT 120, for example, may determine whether a difference between the target transmission duration and the first length is greater than four. Thereafter, the method 2600 may proceed to block 2655, where the UT 120 can include an end-of-frame padding subframe in the A-MPDU frame when the difference is greater than four. Optionally, the UT 120 can increment the first length by four for each end-of-frame padding subframe included in the padding information. After block 2655, the method 2600 may return to block 2650. Optionally, after block 2650, the method 2600 may return to block 2610.

Additionally or alternatively, after block 2610, 2630, 2640, or 2650, the method 2600 may proceed to block 2660, where the UT 120, for example, may determine whether the first length is less than the target transmission duration. Thereafter, the method 2600 may proceed to block 2665, where the UT 120 can include a final end-of-frame padding subframe in the A-MPDU frame. In some implementations, the UT 120 can include an octet of padding in the final end-of-frame padding subframe when the first length is less than the target transmission duration. Optionally, the UT 120 can increment the first length by one for each octet of padding included in the final end-of-frame padding subframe. After block 2665, the method 2600 may return to block 2660. Optionally, after block 2660, the method 2600 may return to block 2610.

In some aspects, as part of method 2600, the UT 120, for example, can transmit the PSDU concurrently with a plurality of UTs 120 (e.g., UTs 120A-D) over the target transmission duration. In some aspects, a transmission power level of the transmitted PSDU is substantially constant during the target transmission duration. In some aspects, the UT 120, for example, may utilize a transmission data rate, indicated in the message, for transmitting the PSDU. In some aspects, the UT 120, for example, may utilize a level of aggregation, indicated in the message, for transmitting the PSDU. In some aspects, the UT 120, for example, may utilize an uplink transmission opportunity, determined by the user terminal during a setup phase, for transmitting the PSDU. In an embodiment, the PSDU can be transmitted within a PHY convergence protocol data unit (PPDU).

In some embodiments, a UT 120 for wireless communication may perform one or more of the functions of methods 2400, 2500, 2600, in accordance with certain embodiments described herein. The UT 120 may comprise means for receiving a message. In certain embodiments, the means for receiving can be implemented by the receiver 312, the processor 304, the antenna 316, the DSP 320, and/or the signal detector 318 (FIG. 3). The UT 120 may comprise means for generating an aggregated medium access control (MAC) packet data unit (A-MPDU) frame. In certain embodiments, the means for generating can be implemented by the transmitter 310, the processor 304, the antenna 316, the DSP 320, and/or the signal detector 318 (FIG. 3).

The UT 120 may further comprise means for determining whether an additional A-MPDU subframe having a second length may be added to the A-MPDU frame. In certain embodiments, the means for generating for transmission to the plurality of receiving devices can be implemented by the receiver 312, the processor 304, the antenna 316, the DSP 320, and/or the signal detector 318 (FIG. 3).

The UT 120 may further comprise means for including one or more padding subframes in the A-MPDU frame. In certain embodiments, the means for including can be implemented by the receiver 312, the transmitter 310, the processor 304, the antenna 316, the DSP 320, and/or the signal detector 318 (FIG. 3). The UT 120 may comprise means for generating the PSDU. In certain embodiments, the means for generating can be implemented by the transmitter 310, the processor 304, the antenna 316, the DSP 320, and/or the signal detector 318 (FIG. 3).

The UT 120 may comprise means for transmitting the generated PSDU. In certain embodiments, the means for transmitting can be implemented by the transmitter 310, the processor 304, the antenna 316, the DSP 320, and/or the signal detector 318 (FIG. 3).

A person/one having ordinary skill in the art would understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

While the foregoing is directed to aspects of the present disclosure, other and further aspects of the disclosure may be devised without departing from the basic scope thereof, and the scope thereof is determined by the claims that follow.

What is claimed is:

1. A method for wireless communication, comprising:
    receiving, at a user terminal, a trigger frame from an access point including one or more parameters indicating a modulation and coding scheme (MCS) and a level of aggregation;
    determining, at the user terminal, a target transmission duration for transmission of a physical layer (PHY) service data unit (PSDU) to the access point based on the one or more parameters in the trigger frame indicating the MCS;
    generating, at the user terminal, an aggregated medium access control (MAC) packet data unit (A-MPDU) frame comprising at least one A-MPDU subframe, the A-MPDU frame having a first length;
    determining, at the user terminal, whether an additional A-MPDU subframe having a second length may be added to the A-MPDU frame based at least in part on the first length, the second length, and the target transmission duration;
    including one or more padding subframes in the A-MPDU frame based at least in part on a comparison between the first length and the target transmission duration;
    generating, at the user terminal, the PSDU, the PSDU including the A-MPDU frame and the one or more padding subframes; and
    transmitting, at the user terminal, the generated PSDU over the target transmission duration and in accordance with the indicated level of aggregation.

2. The method of claim 1, further comprising:
    determining whether a remainder of the first length divided by four is equal to zero;
    including an octet of padding in the A-MPDU frame when the first length is less than the target transmission duration and the remainder is not equal to zero; and
    incrementing the first length by one for each octet of padding included in the A-MPDU frame.

3. The method of claim 1, further comprising:
determining whether a difference between the target transmission duration and the first length is greater than four;
including an end-of-frame padding subframe in the A-MPDU frame when the difference is greater than four; and
incrementing the first length by four for each end-of-frame padding subframe included in the A-MPDU frame.

4. The method of claim 1, further comprising:
including a final end-of-frame padding subframe in the A-MPDU frame;
including an octet of padding in the final end-of-frame padding subframe when the first length is less than the target transmission duration; and
incrementing the first length by one for each octet of padding included in the final end-of-frame padding subframe.

5. The method of claim 1, further comprising:
transmitting the PSDU concurrently with a plurality of user terminals over the target transmission duration.

6. The method of claim 1, wherein the one or more parameters further indicate a transmission power level.

7. The method of claim 1, wherein a transmission power level of the transmitted PSDU is substantially constant during the target transmission duration.

8. The method of claim 1, further comprising:
adding a plurality of bits to the A-MPDU frame sufficient to increase the first length to be equal to the target transmission duration.

9. The method of claim 8, wherein the plurality of bits comprises at least one of:
an end-of-frame padding delimiter;
a subframe pad octet; and
an aggregated medium access control protocol data unit end-of-frame subframe.

10. The method of claim 1, further comprising:
utilizing an uplink transmission opportunity, determined by the user terminal during a setup phase, for transmitting the PSDU.

11. The method of claim 1, wherein the trigger frame is a clear to transmit (CTX) message, and wherein the PSDU is transmitted within a PHY convergence protocol data unit (PPDU).

12. A user terminal for wireless communication, comprising:
a receiver configured to receive a trigger frame from an access point including one or more parameters indicating a modulation and coding scheme (MCS) and a level of aggregation;
a processor configured to:
determine a target transmission duration for transmission of a physical layer (PHY) service data unit (PSDU) to the access point based on the one or more parameters in the trigger frame indicating the MCS,
generate an aggregated medium access control (MAC) packet data unit (A-MPDU) frame comprising at least one A-MPDU subframe, the A-MPDU frame having a first length,
determine whether an additional A-MPDU subframe having a second length may be added to the A-MPDU frame based at least in part on the first length, the second length, and the target transmission duration,
include one or more padding subframes in the A-MPDU frame based at least in part on a comparison between the first length and the target transmission duration, and
generate the PSDU, the PSDU including the A-MPDU frame and the one or more padding subframes; and
a transmitter configured to transmit the generated PSDU over the target transmission duration and in accordance with the indicated level of aggregation.

13. The user terminal of claim 12, wherein the processor is further configured to:
determine whether a remainder of the first length divided by four is equal to zero;
include an octet of padding in the A-MPDU frame when the first length is less than the target transmission duration and the remainder is not equal to zero; and
increment the first length by one for each octet of padding included in the A-MPDU frame.

14. The user terminal of claim 12, wherein the processor is further configured to:
determine whether a difference between the target transmission duration and the first length is greater than four;
include an end-of-frame padding subframe in the A-MPDU frame when the difference is greater than four; and
increment the first length by four for each end-of-frame padding subframe included in the A-MPDU frame.

15. The user terminal of claim 12, wherein the processor is further configured to:
include a final end-of-frame padding subframe in the A-MPDU frame;
include an octet of padding in the final end-of-frame padding subframe when the first length is less than the target transmission duration; and
increment the first length by one for each octet of padding included in the final end-of-frame padding subframe.

16. The user terminal of claim 12, wherein the transmitter is further configured to transmit the PSDU concurrently with a plurality of user terminals over the target transmission duration.

17. The user terminal of claim 12, wherein the one or more parameters further indicate a transmission power level.

18. The user terminal of claim 12, wherein a transmission power level of the transmitted PSDU is substantially constant during the target transmission duration.

19. The user terminal of claim 12, wherein the processor is further configured to add a plurality of bits to the A-MPDU frame sufficient to increase the first length to be equal to the target transmission duration.

20. The user terminal of claim 19, wherein the plurality of bits comprises at least one of:
an end-of-frame padding delimiter;
a subframe pad octet; and
an aggregated medium access control protocol data unit end-of-frame subframe.

21. The user terminal of claim 12, wherein the transmitter is further configured to utilize an uplink transmission opportunity, determined during a setup phase, for transmitting the PSDU, wherein the trigger frame is a clear to transmit (CTX) message.

22. A user terminal for wireless communication, comprising:
means for receiving a trigger frame from an access point including one or more parameters indicating a modulation and coding scheme (MCS) and a level of aggregation;
means for determining a target transmission duration for transmission of a physical layer (PHY) service data unit (PSDU) to the access point based on the one or more parameters in the trigger frame indicating the MCS;

means for generating an aggregated medium access control (MAC) packet data unit (A-MPDU) frame comprising at least one A-MPDU subframe, the A-MPDU frame having a first length;
means for determining whether an additional A-MPDU subframe having a second length may be added to the A-MPDU frame based at least in part on the first length, the second length, and the target transmission duration;
means for including one or more padding subframes in the A-MPDU frame based at least in part on a comparison between the first length and the target transmission duration;
means for generating the PSDU, the PSDU including the A-MPDU frame and the one or more padding subframes; and
means for transmitting the generated PSDU over the target transmission duration and in accordance with the indicated level of aggregation.

23. The user terminal of claim 22, further comprising:
means for determining whether a remainder of the first length divided by four is equal to zero;
means for including an octet of padding in the A-MPDU frame when the first length is less than the target transmission duration and the remainder is not equal to zero; and
means for incrementing the first length by one for each octet of padding included in the A-MPDU frame.

24. The user terminal of claim 22, further comprising:
means for determining whether a difference between the target transmission duration and the first length is greater than four;
means for including an end-of-frame padding subframe in the A-MPDU frame when the difference is greater than four; and
means for incrementing the first length by four for each end-of-frame padding subframe included in the A-MPDU frame.

25. The user terminal of claim 22, further comprising:
means for including a final end-of-frame padding subframe in the A-MPDU frame;
means for including an octet of padding in the final end-of-frame padding subframe when the first length is less than the target transmission duration; and
means for incrementing the first length by one for each octet of padding included in the final end-of-frame padding subframe.

26. The user terminal of claim 22, further comprising:
means for transmitting the PSDU concurrently with a plurality of user terminals over the target transmission duration.

27. The user terminal of claim 22, wherein the one or more parameters further indicate a transmission power level.

28. The user terminal of claim 22, wherein a transmission power level of the transmitted PSDU is substantially constant during the target transmission duration.

29. The user terminal of claim 22, further comprising:
means for adding a plurality of bits to the A-MPDU frame sufficient to increase the first length to be equal to the target transmission duration.

30. The user terminal of claim 29, wherein the plurality of bits comprises at least one of:
an end-of-frame padding delimiter;
a subframe pad octet; and
an aggregated medium access control protocol data unit end-of-frame subframe.

31. The user terminal of claim 22, further comprising:
means for utilizing an uplink transmission opportunity, determined during a setup phase, for transmitting the PSDU, wherein the trigger frame is a clear to transmit (CTX) message.

32. A non-transitory computer readable medium comprising instructions that, when executed, perform a method of communication, the method comprising:
receiving, at a user terminal, a trigger frame from an access point including one or more parameters indicating a modulation and coding scheme (MCS) and a level of aggregation;
determining a target transmission duration for transmission of a physical layer (PHY) service data unit (PSDU) to the access point based on the one or more parameters in the trigger frame indicating the MCS;
generating an aggregated medium access control (MAC) packet data unit (A-MPDU) frame comprising at least one A-MPDU subframe, the A-MPDU frame having a first length;
determining whether an additional A-MPDU subframe having a second length may be added to the A-MPDU frame based at least in part on the first length, the second length, and the target transmission duration;
including one or more padding subframes in the A-MPDU frame based at least in part on a comparison between the first length and the target transmission duration;
generating the PSDU, the PSDU including the A-MPDU frame and the one or more padding subframes; and
transmitting the generated PSDU from the user terminal over the target transmission duration and in accordance with the indicated level of aggregation.

33. The non-transitory computer readable medium of claim 32, wherein the method further comprises:
determining whether a remainder of the first length divided by four is equal to zero;
including an octet of padding in the A-MPDU frame when the first length is less than the target transmission duration and the remainder is not equal to zero; and
incrementing the first length by one for each octet of padding included in the A-MPDU frame.

34. The non-transitory computer readable medium of claim 32, wherein the method further comprises:
determining whether a difference between the target transmission duration and the first length is greater than four;
including an end-of-frame padding subframe in the A-MPDU frame when the difference is greater than four; and
incrementing the first length by four for each end-of-frame padding subframe included in the padding information.

35. The non-transitory computer readable medium of claim 32, wherein the method further comprises:
including a final end-of-frame padding subframe in the A-MPDU frame;
including an octet of padding in the final end-of-frame padding subframe when the first length is less than the target transmission duration; and
incrementing the first length by one for each octet of padding included in the final end-of-frame padding subframe.

36. The non-transitory computer readable medium of claim 32, wherein the method further comprises:
transmitting the PSDU concurrently with a plurality of user terminals over the target transmission duration.

37. The non-transitory computer readable medium of claim 32, wherein the one or more parameters further indicate a transmission power level.

38. The non-transitory computer readable medium of claim 32, wherein a transmission power level of the transmitted PSDU is substantially constant during the target transmission duration.

39. The non-transitory computer readable medium of claim 32, wherein the method further comprises:
   adding a plurality of bits to the A-MPDU frame sufficient to increase the first length to be equal to the target transmission duration.

40. The non-transitory computer readable medium of claim 39, wherein the plurality of bits comprises at least one of:
   an end-of-frame padding delimiter;
   a subframe pad octet; and
   an aggregated medium access control protocol data unit end-of-frame subframe.

41. The non-transitory computer readable medium of claim 32, wherein the method further comprises:
   utilizing an uplink transmission opportunity, determined by the user terminal during a setup phase, for transmitting the PSDU.

42. The non-transitory computer readable medium of claim 32, wherein the PSDU is transmitted within a PHY convergence protocol data unit (PPDU).

* * * * *